(12) United States Patent
Wang et al.

(10) Patent No.: US 8,044,097 B2
(45) Date of Patent: Oct. 25, 2011

(54) CHROMAN DERIVATIVES

(75) Inventors: Bing Wang, Cupertino, CA (US); Jian Chen, Sunnyvale, CA (US)

(73) Assignee: Ampere Life Sciences, Inc., Mountain View, CA (US)

( * ) Notice: Subject to any disclaimer, the term of this patent is extended or adjusted under 35 U.S.C. 154(b) by 240 days.

(21) Appl. No.: 12/393,836

(22) Filed: Feb. 26, 2009

(65) Prior Publication Data

US 2009/0192179 A1    Jul. 30, 2009

Related U.S. Application Data

(62) Division of application No. 10/941,125, filed on Sep. 15, 2004, now Pat. No. 7,514,461.

(60) Provisional application No. 60/504,391, filed on Sep. 19, 2003, provisional application No. 60/541,737, filed on Feb. 4, 2004.

(51) Int. Cl.
  *A61K 31/353* (2006.01)
  *A61K 31/4433* (2006.01)
  *C07D 311/72* (2006.01)
  *C07D 405/04* (2006.01)

(52) U.S. Cl. .............. 514/456; 514/337; 546/282.7; 549/23; 549/365; 549/408; 549/410

(58) Field of Classification Search .......... 549/23, 549/365, 408, 410; 546/282.7; 514/337, 514/456
See application file for complete search history.

(56) References Cited

U.S. PATENT DOCUMENTS

| | | |
|---|---|---|
| 3,574,627 A | 4/1971 | Stern at al. |
| 3,801,603 A | 4/1974 | Hartmann at al. |
| 4,360,532 A | 11/1982 | Sundeen |
| 4,452,801 A | 6/1984 | Sundeen |
| 4,511,685 A | 4/1985 | Nissen et al. |
| 4,515,975 A | 5/1985 | Vogel et al. |
| 4,645,845 A | 2/1987 | Gehrken et al. |
| 4,716,238 A | 12/1987 | Timár et al. |
| 4,728,650 A | 3/1988 | Eziri et al. |
| 4,780,469 A | 10/1988 | Toda et al. |
| 4,814,346 A | 3/1989 | Albert et al. |
| 4,877,810 A | 10/1989 | Mickle et al. |
| 4,950,684 A | 8/1990 | Koszyk et al. |
| 5,015,661 A | 5/1991 | Walser |
| 5,059,609 A | 10/1991 | Eggler et al. |
| 5,082,849 A | 1/1992 | Huang et al. |
| 5,093,353 A | 3/1992 | Koszyk et al. |
| 5,099,012 A | 3/1992 | Wu et al. |
| 5,132,310 A | 7/1992 | Walser |
| 5,155,130 A | 10/1992 | Stanton et al. |
| 5,250,547 A | 10/1993 | Lochead et al. |
| 5,260,294 A | 11/1993 | Walser |
| 5,290,797 A | 3/1994 | Le Baut et al. |
| 5,326,771 A | 7/1994 | Heine et al. |
| 5,350,751 A | 9/1994 | Wagner et al. |
| 5,385,931 A | 1/1995 | Bigg et al. |
| 5,393,775 A | 2/1995 | Le Baut et al. |
| 5,395,834 A | 3/1995 | Le Baut et al. |
| 5,424,321 A | 6/1995 | Hellberg et al. |
| 5,484,810 A | 1/1996 | Grisar et al. |
| 5,500,444 A | 3/1996 | Grisar et al. |
| 5,534,536 A | 7/1996 | Ohuchida et al. |
| 5,541,199 A | 7/1996 | Mewshaw |
| 5,591,772 A | 1/1997 | Lane et al. |
| 5,607,966 A | 3/1997 | Hellberg et al. |
| 5,646,149 A | 7/1997 | Hellberg et al. |
| 5,663,294 A | 9/1997 | Colman et al. |
| 5,670,667 A | 9/1997 | Mewshaw |
| 5,672,710 A | 9/1997 | Beard et al. |
| 5,684,039 A | 11/1997 | Mewshaw |
| 5,719,180 A | 2/1998 | Shudo et al. |
| 5,747,528 A | 5/1998 | Trivedi |
| 5,750,544 A | 5/1998 | Ohuchida et al. |
| 5,756,521 A | 5/1998 | Mewshaw |
| 5,811,438 A | 9/1998 | Hellberg et al. |
| 5,821,130 A | 10/1998 | Baldwin et al. |

(Continued)

FOREIGN PATENT DOCUMENTS

DE    3842029 A1    6/1990

(Continued)

OTHER PUBLICATIONS

Christen, S. et al. (Apr. 1997). "γ-Tocopherol Traps Mutagenic Electrophiles Such as $NO_x$ and Complements α-Tocopherol: Physiological Implications," *Proc. Natl. Acad. Sci.* 94:3217-3222.

Dallaker, F. et al. (1991). "Derivatives of the Vitamin E series.2. Preparation of All-Rac-5-Prenyl-γ-Tocopherol," *Chemiker Zeitung* 115(10):258-289. (Abstract Only).

Fryer, M.J. (1998). "Vitamin E Status and Neurodegenerative Disease," *Nutritional Neuroscience* 1:327-351.

(Continued)

*Primary Examiner* — Bernard Dentz
(74) *Attorney, Agent, or Firm* — Morrison & Foerster LLP

(57) ABSTRACT

The invention relates to novel chroman derivatives, stereoisomers and pharmaceutically acceptable salts of Formula I

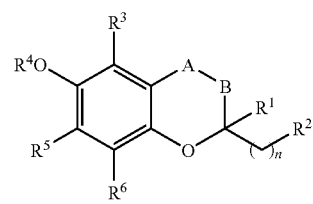

Formula I wherein the substituents are as defined in the specification. They are useful in the treatment of disorders mediated by lipoxygenase, such as immune diseases, respiratory diseases and cardiovascular diseases, as well as in the treatment of neurodegenerative disorders and/or mitochondria) disorders. They are also useful in the manufacture of pharmaceutical formulations for the treatment of such conditions.

11 Claims, No Drawings

U.S. PATENT DOCUMENTS

| | | | |
|---|---|---|---|
| 5,821,264 | A | 10/1998 | Lane et al. |
| 5,846,988 | A | 12/1998 | Hellberg |
| 5,849,755 | A | 12/1998 | Englert et al. |
| 5,874,461 | A | 2/1999 | de Chaffoy de Courcelles et al. |
| 5,925,673 | A | 7/1999 | Hellberg et al. |
| 5,981,530 | A | 11/1999 | Ogata et al. |
| 5,981,572 | A | 11/1999 | Ellis et al. |
| 5,990,142 | A | 11/1999 | Carganico et al. |
| 6,034,256 | A | 3/2000 | Carter et al. |
| 6,133,277 | A | 10/2000 | Wingerinck et al. |
| 6,150,402 | A | 11/2000 | Wechter et al. |
| 6,222,051 | B1 | 4/2001 | Lee et al. |
| 6,235,774 | B1 | 5/2001 | Fahrig et al. |
| 6,242,479 | B1 | 6/2001 | Wechter |
| 6,331,532 | B1 | 12/2001 | Murphy et al. |
| 6,331,561 | B2 | 12/2001 | Fahrig et al. |
| 6,342,602 | B1 | 1/2002 | Teng et al. |
| 6,387,899 | B1 | 5/2002 | Berg et al. |
| 6,410,589 | B2 | 6/2002 | Wechter |
| 6,417,223 | B1 | 7/2002 | Sanders et al. |
| 6,479,497 | B1 | 11/2002 | Berg et al. |
| 6,498,191 | B2 | 12/2002 | Ghosh et al. |
| 6,511,966 | B2 | 1/2003 | Ghosh et al. |
| 6,518,250 | B2 | 2/2003 | Yoshikawa et al. |
| 6,555,575 | B2 | 4/2003 | Wechter |
| 6,596,745 | B2 | 7/2003 | Gall |
| 6,645,998 | B2 | 11/2003 | Sanders et al. |
| 7,470,798 | B2 | 12/2008 | Wang et al. |
| 2001/0018530 | A1 | 8/2001 | Fahrig et al. |
| 2002/0016359 | A1 | 2/2002 | Hellberg et al. |
| 2002/0052342 | A1 | 5/2002 | Murphy et al. |
| 2002/0082292 | A1 | 6/2002 | Sahoo et al. |
| 2002/0127252 | A1 | 9/2002 | Kramer et al. |
| 2003/0069208 | A1 | 4/2003 | Murphy et al. |
| 2003/0100603 | A1 | 5/2003 | Beinlich et al. |
| 2003/0103895 | A1 | 6/2003 | Cyr et al. |
| 2003/0103899 | A1 | 6/2003 | Cyr |
| 2003/0176448 | A1 | 9/2003 | Ghosh et al. |
| 2003/0233002 | A1 | 12/2003 | Kanter et al. |
| 2004/0097433 | A1 | 5/2004 | Boddupalli et al. |
| 2005/0065099 | A1 | 3/2005 | Walkinshaw et al. |

FOREIGN PATENT DOCUMENTS

| | | |
|---|---|---|
| EP | 0 535 283 A1 | 4/1993 |
| JP | 48092372 A2 | 11/1973 |
| JP | 62292777 A | 12/1987 |
| JP | 10-251247 A2 | 9/1998 |
| WO | WO-87/05020 A1 | 8/1987 |
| WO | WO-96/16957 A1 | 6/1996 |
| WO | WO-01/05781 A1 | 1/2001 |

OTHER PUBLICATIONS

Jauslin, M.L. (e-pub. Aug. 15, 2003). "Mitochondria-Targeted Antioxidants protect Friedreich Ataxia Fibroblasts from Endogenous Oxidative Stress More Effectively than Untargeted Antioxidants," *FASEB Journal* 10.1096/fj.03-240.fje.

Kelso, G.F. et al. (2002). "Prevention of Mitochondrial Oxidative Damage Using Targeted Antioxidants," *Annals of the New York Academy of Sciences* 959:263-274.

Lang, D. (2002). "Cardiac Hypertrophy and Oxidative Stress: A Leap of Faith or Stark Reality?" *Heart* 87:316-318.

Skinner, W.A. et al. (Jul. 1967). "Structure-Activity Relations in the Vitamin E Series. I. Effects of 5-Methyl Substitution on 6-Hydroxy-2,2,5,7,8-Pentamethylchroman," *Journal of Medicinal Chemistry* 10(4):657-661.

Smith, R.A.J. et al. (Apr. 29, 2003). "Delivery of Bioactive Molecules to Mitochondria in vivo," *PNAS* 100(9):5407-5412.

Wolf, H. et al. (1981). "Protektiver Effekt der Antioxidativ Wirksamen Chromanstruktur des Tocopherols Auf die Folgen Stimulierter Arachidonsäure-Freisetzung in der Pulmonalen Strombahn," *Klinsche Wochenschrift* 59:463-465. (Translation of Abstract Only).

Wolf, H.R.D. et al. (1982). "Experimental and Clinical Results in Shock Lung Treatment with Vitamin E," *Annals of the New York Academy of Sciences* 393:392-410.

CHROMAN DERIVATIVES

CROSS-REFERENCE TO RELATED APPLICATIONS

This U.S. patent application is a divisional of U.S. patent application Ser. No. 10/941,125 filed Sep. 15, 2004 which claims priority under 35 U.S.C. 119(e) to U.S. Provisional Application Ser. No. 60/504,391, filed Sep. 19, 2003, and Ser. No. 60/541,737, filed Feb. 4, 2004. All of these applications are incorporated herein by reference in their entirety.

BACKGROUND INFORMATION

The present invention relates to certain novel chroman derivatives of Formula I as depicted below, pharmaceutical formulations containing them, and their uses as therapeutic agents, and syntheses therefor. Their uses as therapeutic agents that may act as lipoxygenase inhibitors include but is not limited to prevention or treatment of diseases involving apoptosis in cancer cells; diseases involving hypoxia, or anoxia; diseases involving inflammation; disorders of the airways; diseases involving neurodegeneration and neuroinflammation; and diseases involving the autoimmune system.

The use of certain chroman-ylmethylamino derivatives for the treatment of Parkinson's disease and epilepsy has been disclosed in U.S. Pat. Nos. 5,663,294; 5,541,199; 5,670,667; 5,684,039; 5,756,521; 6,235,774; and 6,331,561. The use of chromans for treating mitochondria associated diseases including Alzheimer's disease, diabetes mellitus, Parkinson's disease, neuronal and cardiac ischemia, Huntington's disease, and stroke is disclosed in U.S. Pat. Nos. 6,498,191 and 6,511,966 and US patent application US 2003/0176448. Triphenyl phosphonium tocopherol analogs having cardioprotective or mitochondrially targeted antioxidant properties have been described by Gisar, J M in EP 545,283 and by Murphy, M. in *Annals of the New York Academy of Sciences* (2002), 959, 263-274 and in U.S. Pat. No. 6,331,532, US 2202/00523242 and US 2003/0069208.

The use of antioxidants targeted to mitochondria shown to be effective at slowing disease progression has been reported by Jauslin, M L in *FASEB Journal*, express article 10.1096/fj.03-0240fje. Therapeutic benefit of administering γ-tocopherol derivatives and metabolites as antioxidants and nitrogen oxide scavengers which treat high blood pressure, thromboembolic diseases, cardiovascular disease, cancer, natriuretic disease, formation of neuropathological lesion and reduced immune system response are disclosed in U.S. Pat. Nos. 6,555,575; 6,24,479; 6,150,402; and 6,410,589. The use of certain chroman derivatives in cosmetic and dermatological preparations is disclosed in US 2002/0127252. Beneficial effects of Vitamin E in the progression of a number of major degenerative diseases of the nervous system is examined in Fryer, *Nutritional Neuroscience*, (1998) Vol. 1, 327-351. Reduction of the inflammation marker CRP with 6-hydroxy chromans and with tocopherols has been disclosed in commonly owned U.S. patent applications 60/426,764 and US 2003/0100603.

The use of chromans as lipoxygenase inhibitors has been disclosed for example in U.S. Pat. No. 5,059,609, U.S. Pat. No. 4,950,684, U.S. Pat. No. 5,015,661, U.S. Pat. No. 4,780,469, U.S. Pat. No. 5,591,772; U.S. Pat. No. 5,925,673; U.S. Pat. No. 5,250,547; U.S. Pat. No. 5,393,775; and U.S. Pat. No. 4,814,346.

SUMMARY OF THE INVENTION

The present invention is concerned with certain novel chroman derivatives of Formula I, which may be useful in the manufacture of pharmaceutical compositions for treating disorders mediated by lipoxygenases.

In a first aspect, the present invention concerns the compounds represented by a general Formula I selected from the groups i), ii), and iii)

i)

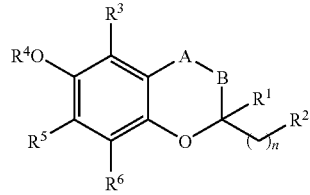

Formula I wherein:
-A-B— is —$CH_2$—$CH_2$—; —CH=CH—; —$CH_2$—O—; —$CH_2$—S—; or —$CH_2$—N—;

n is 0;

$R^1$ is $C_{1-4}$ alkyl;

$R^2$ is $C_{1-4}$ alkyl;

$R^3$ is
—$(CR_2)_m$C(O)$OR^a$;
—$(CR_2)_m$N(OH)C(O)$NR^bR^c$;
—$(CR_2)_m NR^bR^c$;
—$(CR_2)_m NR^b$—$SO_2$—$R^a$;
—$(CR_2)_m SO_2 NR^bR^c$;
—$(CR_2)_m$P(O)$(OR)_2$;
—CR=Het, wherein Het is a saturated, partially unsaturated or unsaturated heterocyclyl optionally substituted with one or more substituents selected from alkyl, haloalkyl, hydroxy, alkoxy, halogen, oxo, cyano, nitro, amino, —$SO_2NR_2$, and —C(O)OR;

cycloalkyl, aryl, or saturated, partially unsaturated or unsaturated heterocyclyl, all rings optionally substituted with one or more substituents selected from alkyl, haloalkyl, hydroxy, alkoxy, halogen, oxo, cyano, nitro, amino, —$SO_2NR_2$, and —C(O)OR, with the proviso that the heterocyclyl is not 4,5-dihydro-isoxazol-3-yl or chroman; or haloalkenyl $R^4$ is hydrogen; optionally substituted $C_{1-4}$ alkyl; $C_{2-12}$ alkenyl; hydroxyalkyl; acyl; glucoside; phosphoryl; phosphoryloxyalkyl; carboxyalkylcarbonyl; aminoalkylcarbonyl; or alkylketocarbonyl;

$R^5$ and $R^6$ are independently of each other $C_{1-6}$ alkyl, $C_{2-12}$ alkenyl, or halogen;

m is 0 to 3;

R is hydrogen or $C_{1-4}$ alkyl;

$R^a$ is hydrogen; optionally substituted $C_1$, alkyl; optionally substituted $C_{2-12}$ alkenyl; optionally substituted aryl; optionally substituted cycloalkyl; or optionally substituted saturated, partially unsaturated or unsaturated heterocyclyl;

$R^b$ and $R^c$ are independently of each other hydrogen; $C_{1-4}$ alkyl; hydroxyalkyl; aminoalkyl; optionally substituted aryl; optionally substituted benzyl; or optionally substituted heterocyclyl;

with the proviso that if $R^5$ or $R^6$ are halogen, then $R^3$ is not hydrogen or methyl;

ii)

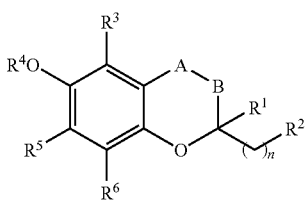

Formula I wherein:
-A-B— is —$CH_2$—$CH_2$—; —CH=CH—; —$CH_2$—O—; —$CH_2$—S—; or —$CH_2$—N—;
n is 0 to 5;
$R^1$ is $C_{1-4}$ alkyl or halo-($C_{1-4}$)-alkyl;
$R^2$ is
  —C(O)$OR^a$;
  halogen or dihalovinyl;
  aryl optionally substituted with substituted with one or more substituents selected from alkyl, haloalkyl, hydroxy, alkoxy, halogen, oxo, cyano, nitro, amino, —$SO_2NR_2$, and —C(O)OR;
  -Het, —CH-(Het)$_2$; or —CH=Het; where Het is saturated, partially unsaturated or unsaturated heterocyclyl Het is saturated, partially unsaturated or unsaturated heterocyclyl optionally substituted with one or more substituents selected from alkyl, haloalkyl, hydroxy, alkoxy, halogen, oxo, cyano, nitro, amino, —$SO_2NR_2$, and —C(O)OR;
$R^3$ is
  hydrogen;
  halogen;
  optionally substituted $C_{1-6}$ alkyl;
  $C_{2-20}$ alkenyl;
  nitro;
  —OR;
  —$(CR_2)_m$C(O)$OR^a$;
  —$(CR_2)_m$C(O)$NR^bR^c$;
  —$(CR_2)_m$N(OH)C(O)$NR^bR^c$;
  —$(CR_2)_m NR^bR^c$;
  —(CR2)$_m NR^b$—$SO_2$—$R^a$;
  —(CR2)$_m$S(O)$_{0-2}R^a$;
  (CR2)$_m SO_2NR^bR^c$;
  —CR=Het, wherein Het is a saturated, partially unsaturated or unsaturated heterocyclyl optionally substituted with one or more substituents selected from alkyl, haloalkyl, hydroxy, alkoxy, halogen, oxo, cyano, nitro, amino, —$SO_2NR_2$, and —C(O)OR;
  cycloalkyl, aryl or saturated, partially unsaturated or unsaturated heterocyclyl, all rings optionally substituted with $C_{1-6}$ alkyl, hydroxy, alkoxy, nitro, amino, or —C(O)OR;
$R^4$ is hydrogen; optionally substituted $C_{1-4}$ alkyl, $C_{2-12}$ alkenyl, hydroxyalkyl, acyl, glucoside, phosphoryl, phosphoryloxyalkyl, carboxyalkylcarbonyl, aminoalkylcarbonyl, or alkylketocarbonyl;
$R^5$ and $R^6$ are independently of each other $C_{1-6}$ alkyl, $C_{2-20}$ alkenyl, or halogen;
m is 0 to 3;
R is hydrogen or $C_{1-4}$ alkyl;
$R^a$ is hydrogen, optionally substituted $C_{1-4}$ alkyl, optionally substituted $C_{2-12}$ alkenyl, optionally substituted aryl, optionally substituted cycloalkyl, or optionally substituted heterocyclyl;
$R^b$ and $R^c$ are independently of each other hydrogen, $C_{1-4}$ alkyl, hydroxyalkyl, aminoalkyl, optionally substituted aryl, optionally substituted benzyl, or optionally substituted heterocyclyl; or $R^b$ and $R^c$ taken together with the atom to which they are attached may form a 5 to 8 membered aromatic, saturated or unsaturated ring, optionally incorporating one additional atom chosen from N, O, or S and optionally substituted with a substituent selected from the group consisting of lower alkyl, halo, cyano, alkylthio, lower alkoxy, oxo, phenyl, benzyl and carboxy;
with the proviso that if -A-B— is —$CH_2$—$CH_2$— or —CH=CH—, and $R^3$, $R^5$, or $R^6$ are hydrogen or $C_{1-3}$-alkyl then $R^2$ is not —C(O)OR, halogen, or aryl;
further provided that if $R^2$ is -Het and $R^3$ is $C_{1-6}$-alkyl, then n=0 and Het is not 2,2-dimethyl-[1,3]dioxolan-4-yl, oxiran-2-yl, thiazole-2-yl, oxazole-2-yl, thiazole-4-yl or benzofuran-2-yl;
and further provided that if $R^2$ is aryl, then $R^3$ is not optionally substituted alkyl;
or
iii)

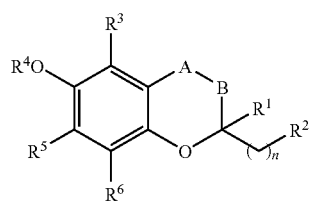

Formula I wherein:
-A-B— is —$CH_2$—$CH_2$—; —CH=CH—; —$CH_2$—O—; —$CH_2$—S—; or —$CH_2$—N—;
n is 0;
$R^1$ is $C_1$ alkyl;
$R^2$ is $C_{1-20}$ alkyl or $C_{2-20}$ alkenyl;
$R^3$ is —$(CR_2)_m$S(O)$_{0-2}R^a$; wherein $R^a$ is hydrogen; $C_{1-4}$ alkyl; —$(CR_2)_m$C(O)OR; —$(CR_2)_m$C(O)NR'R'; optionally substituted $C_{2-12}$ alkenyl; optionally substituted aryl; optionally substituted cycloalkyl; or optionally substituted saturated, partially saturated, or unsaturated heterocyclyl, with the proviso that $R^a$ is not ethyl or —$(CR_2)_2$C(O)O$C_2H_5$; if $R^1$ and $R^2$ are methyl;
$R^4$ is hydrogen; optionally substituted $C_{1-4}$ alkyl; $C_{2-12}$ alkenyl; hydroxyalkyl; acyl; glucoside; phosphoryl; phosphoryloxyalkyl; carboxyalkylcarbonyl; aminoalkylcarbonyl; or alkylketocarbonyl;
$R^5$ and $R^6$ are independently of each other $C_{1-6}$ alkyl or $C_{2-12}$ alkenyl;
m is 0 to 3
R is hydrogen or $C_{1-4}$ alkyl
R' and R" are independently of each other hydrogen, $C_{1-4}$ alkyl, hydroxyalkyl, aminoalkyl, optionally substituted aryl, optionally substituted benzyl or optionally substituted heterocyclyl; or $R^b$ and $R^c$ taken together with the atom to which they are attached may form a 5 to 8 membered aromatic, saturated or unsaturated ring, optionally incorporating one additional atom chosen from N, O, or S and optionally substituted with a substituent selected from the group consisting of lower alkyl, halo, cyano, alkylthio, lower alkoxy, oxo, phenyl, benzyl and carboxy;
or
single stereoisomers, mixtures of stereoisomers, or pharmaceutically acceptable salts thereof.

In a preferred embodiment the compound is selected from Formula I group (i), and single stereoisomers, mixtures of stereoisomers, or pharmaceutically acceptable salts thereof, preferably $R^5$ and $R^6$ are $C_{1-4}$ alkyl and $R^4$ is hydrogen, and more preferably $R^1$, $R^2$, $R^5$ and $R^6$ are methyl and $R^4$ is hydrogen. In another embodiment, $R^3$ is aryl or saturated, partially saturated or unsaturated heterocyclyl both optionally substituted with one or more substituents selected from alkyl, haloalkyl, hydroxy, alkoxy, halogen, oxo, cyano, nitro, amino, —SO$_2$NR$_2$ and —C(O)OR. In another embodiment, $R^3$ is —CR=Het and Het is an unsaturated heterocyclyl optionally substituted with one or more substituents selected from alkyl, haloalkyl, hydroxy, alkoxy, halogen, oxo, cyano, nitro, amino, —SO$_2$NR$_2$, and —C(O)OR In another preferred embodiment the compound is selected from Formula I group (ii), and in another embodiment, $R^2$ is -Het selected from furanyl, thienyl, imidazolyl, thiazolyl, thiazolidine, pyrazolyl, oxazolyl, and thiadiazol-2-yl, optionally substituted with one or more substituents selected from alkyl, haloalkyl, hydroxy, alkoxy, halogen, oxo, cyano, nitro, amino, —SO$_2$NR$_2$, and —C(O)OR. In another embodiment, $R^2$ is —CH-(Het)$_2$ or —CH=Het, optionally substituted with one or more substituents selected from alkyl, haloalkyl, hydroxy, alkoxy, halogen, oxo, cyano, nitro, amino, —SO$_2$NR$_2$, and —C(O)OR, particularly $R^2$ is 2,4-dioxo thiazolidin-5-methylene; 2,4-dioxo-thiazolidin-5-methyl; 3-methyl-5-oxo-4,5-dihydro-1H-pyrazol-4-yl)-methyl; or di-(3-methyl-5-oxo-4,5-dihydro-1H-pyrazol-4-yl)-methyl. In another embodiment n is 0 and $R^2$ is dihalovinyl.

In another preferred embodiment the compound is selected from Formula I group (iii). In a preferred embodiment $R^1$ is methyl and $R^2$ is $C_{16}$alkyl or $C_{16}$ alkenyl and $R^3$ is —(CR$_2$)$_m$SR$^a$; and in another preferred embodiment $R^1$ and $R^2$ are $C_{1-4}$ alkyl and $R^3$ is —(CR$_2$)$_m$SR$^a$.

In another aspect, the invention relates to a pharmaceutical composition containing a therapeutically effective amount of a compound of Formula I, or a pharmaceutically acceptable salt thereof admixed with at least one pharmaceutically acceptable excipient. Particularly preferred are those pharmaceutical compositions wherein the compound of Formula I is selected from the preferred compounds and stereoisomers, mixture of stereoisomers or pharmaceutically acceptable salts thereof.

In another aspect, the invention relates to a method of inhibiting a lipoxygenase enzyme in a subject in need of such inhibition comprising administering to said subject a therapeutically effective amount of a compound of the present invention, particularly, the invention relates to a method of inhibiting 5-Lipoxygenase, 15-Lipoxygenase, and/or 12/15-Lipoxygenase enzymes. In another aspect the invention relates to treating a subject with a lipoxygenase mediated condition, and in a preferred embodiment the invention relates to a method of treating a lipoxygenase mediated disorder, particularly of treating a disorder selected from apoptosis in cancer cells including prostatic cancer, gastric cancer, colorectal or esophageal cancer and airways carcinoma; diseases involving hypoxia, or anoxia including atherosclerosis, myocardial infarction, cardiovascular disease, heart failure (including chronic and congestive heart failure), cerebral ischemia, retinal ischemia, myocardial ischemia, post surgical cognitive dysfunction and other ischemias; diseases involving inflammation, including diabetes, arterial inflammation, inflammatory bowel disease, renal disease, pre-menstrual syndrome, asthma, allergic rhinitis, gout; cardiopulmonary inflammation, rheumatoid arthritis, osteoarthritis, muscle fatigue and disorders of the skin such as acne; disorders of the airways including asthma, chronic bronchitis, human. airway carcinomas, mucus hypersecretion, chronic obstructive pulmonary disease (COPD) and adult respiratory distress syndrome; diseases involving neurodegeneration and neuroinflammation including Alzheimer's, dementia and Parkinson's disease; peripheral neuropathy including spinal chord injury, head injury and surgical trauma, and allograft tissue and organ transplant rejection; diseases involving the autoimmune system including psoriasis, eczema, rheumatoid arthritis, and diabetes; and disorders involving the bone loss or bone formation. In a more preferred embodiment invention relates to a method of treating a lipoxygenase mediated disorder, particularly of treating diabetes, arthritis, rheumatoid arthritis, chronic obstructive pulmonary disease (COPD), asthma, allergic rhinitis, or atherosclerosis.

In another aspect, the invention relates to a method of treating a subject suffering from neurodegenerative disorders, oxidative stress disorders or mitochondrial disorders comprising administering to said subject a therapeutically effective amount of a compound of the invention or stereoisomers, mixture of stereoisomers or pharmaceutically acceptable salts thereof. In another embodiment the subject is suffering from a disorder selected from stroke, cerebral ischemia, retinal ischemia, post-surgical cognitive dysfunctions, peripheral neuropathy/neuropathic pain, spinal cord injury, head injury, and surgical trauma. In another embodiment the subject is suffering from a mitochondrial disorder selected from epilepsy, Parkinsonism or Parkinson's disease, Alzheimer's disease amyotrophic lateral sclerosis (ALS), motor neuron diseases, macular degeneration, mitochondria) myopathy, encephalopathy, lactacidosis, stroke (MELAS), Myoclonic epilepsy with ragged red fibers (MERFF), Friedreich's ataxia and cerebellar ataxias. In another embodiment the subject is suffering from an oxidative stress disorder with inflammatory or autoimmune components selected from diabetes, renal disease, premenstrual syndrome, asthma, chronic obstructive pulmonary disease (COPD), rheumatoid arthritis, osteoarthritis, muscle fatigue, irritable bowel syndrome, inflammatory bowel disease (IBD), premenstrual syndrome (PMS), and intermittent claudication. In another embodiment the subject is suffering from dermatological conditions characterized by oxidative stress, selected from age-related skin damage, damage resulting to the skin from insults such as harmful ultraviolet (UV) radiation, pollution, stress and fatigue, contact dermatitis, skin irritation, skin pigmentation, psoriasis and acne.

Particularly preferred are those methods of treatment and uses in the manufacture of pharmaceutical compositions therefor, wherein the compound of Formula I is selected from selected from:
2,2,7,8-Tetramethyl-5-phenyl-chroman-6-ol;
4-(6-Hydroxy-2,2,7,8-tetramethyl-chroman-5-yl)-benzoic acid methyl ester;
4-(6-Hydroxy-2,2,7,8-tetramethyl-chroman-5-yl)-benzoic acid;
2,2,7,8-Tetramethyl-5-pyridin-4-yl-chroman-6-ol;
2,2,7,8-Tetramethyl-5-pyridin-3-yl-chroman-6-ol;
5-(4-Methanesulfonyl-phenyl)-2,2,7,8-tetramethyl-chroman-6-ol;
5-(4-Dimethylamino-phenyl)-2,2,7,8-tetramethyl-chroman-6-ol;
5-(4-Chloro-phenyl)-2,2,7,8-tetramethyl-chroman-6-ol;
4-(6-Hydroxy-2,2,7,8-tetramethyl-chroman-5-yl)-benzenesulfonamide;
5-(4-Methoxy-phenyl)-2,2,7,8-tetramethyl-chroman-6-ol;
(6-Hydroxy-2,2,7,8-tetramethyl-chroman-5-ylmethyl)-1-hydroxyurea;
2,2,7,8-Tetramethyl-5-(3-nitro-phenyl)-chroman-6-ol;

2,2,7,8-Tetramethyl-5-(4-trifluoromethyl-phenyl)-chroman-6-ol;
5-(4-tert-Butyl-phenyl)-2,2,7,8-tetramethyl-chroman-6-ol;
2,2,7,8-Tetramethyl-5-(3,4,5-trimethoxy-phenyl)-chroman-6-ol;
4-(6-Hydroxy-2,2,7,8-tetramethyl-chroman-5-yl)-benzonitrile;
5-(2,5-Dimethoxy-3,4-dimethyl-phenyl)-2,2,7,8-tetramethyl-chroman-6-ol;
5-(6-Hydroxy-2,2,7,8-tetramethyl-chroman-5-yl)-benzene-1,2,3-triol;
5-(6-Hydroxy-2,2,7,8-tetramethyl-chroman-5-yl)-2,3-dimethyl-benzene-1,4-diol;
5-(2-Chloro-phenyl)-2,2,7,8-tetramethyl-chroman-6-ol;
5-Furan-2-yl-2,2,7,8-tetramethyl-chroman-6-ol;
5-Allylsulfanylmethyl-2,2,8-trimethyl-7-(3-methyl-butyl)-chroman-6-ol;
5-Cyclopentylsulfanylmethyl-2,2,7,8-tetramethyl-chroman-6-ol;
5-Hexylsulfanylmethyl-2,2,7,8-tetramethyl-chroman-6-ol;
5-Allylsulfanylmethyl-2,2,7,8-tetramethyl-chroman-6-ol;
5-(4,6-Dimethyl-pyrimidin-2-ylsulfanylmethyl)-2,2,7,8-tetramethyl-chroman-6-ol;
1-[3-(6-Hydroxy-2,2,7,8-tetramethyl-chroman-5-ylmethylsulfanyl)-2-methyl-propionyl]-pyrrolidine-2-carboxylic acid;
4-(6-Hydroxy-2,2,7,8-tetramethyl-chroman-5-ylmethylene)-5-methyl-2-phenyl-2,4-dihydro-pyrazol-3-one;
4-(6-Hydroxy-2,2,7,8-tetramethyl-chroman-5-ylmethylene)-3-phenyl-4H-isoxazol-5-one;
4-[4-(6-Hydroxy-2,2,7,8-tetramethyl-chroman-5-ylmethylene)-3-methyl-5-oxo-4,5-dihydro-pyrazol-1-yl]-benzoic acid;
4-(6-Hydroxy-2,2,7,8-tetramethyl-chroman-5-ylmethylene)-2-methyl-5-propyl-2,4-dihydro-pyrazol 3-one;
5-Hydroxy-3-(6-hydroxy-2,2,7,8-tetramethyl-chroman-5-ylmethylene)-3H-benzofuran-2-one;
2,5,7,8-Tetramethyl-2-thiophen-2-yl-chroman-6-ol;
2-(2,5-Dimethyl-thiophen-3-yl)-2,5,7,8-tetramethyl-chroman-6-ol;
2-(2,5-Dimethyl-thiophen-3-yl)-2,7,8-trimethyl-chroman-6-ol;
8-Chloro-2-(2,5-dimethyl-thiophen-3-yl)-2,5,7-trimethyl-chroman-6-ol;
5-Chloro-2,7,8-trimethyl-2-thiophen-2-yl-chroman-6-ol;
5-[3-(6-Methoxymethoxy-2,7,8-trimethyl-chroman-2-yl)-propylidene]-thiazolidine-2,4-dione;
5-[3-(6-Hydroxy-2,7,8-trimethyl-chroman-2-yl)-propylidene]-thiazolidine-2,4-dione;
3-[6-Hydroxy-2,7,8-trimethyl-2-(4,8,12-trimethyl-tridecyl)-chroman-5-ylmethylsulfanyl]-2-methyl-propionic acid;
2,7,8-Trimethyl-5-(5-methyl-1H-benzoimidazol-2-ylsulfanylmethyl)-2-(4,8,12-trimethyl-tridecyl)-chroman-6-ol;
2-[6-Hydroxy-2,7,8-trimethyl-2-(4,8,12-trimethyl-tridecyl)-chroman-5-ylmethylsulfanyl]-ethanesulfonic acid;
5-(4,6-Dimethyl-pyrimidin-2-ylsulfanylmethyl)-2,7,8-trimethyl-2-(4,8,12-trimethyl-tridecyl)-chroman-6-ol;
4-[2-(4,8-Dimethyl-tridecyl)-6-hydroxy-2,7,8-trimethyl-chroman-5-ylmethylsulfanyl]-benzoic acid;
1-{3-[6-Hydroxy-2,7,8-trimethyl-2-(4,8,12-trimethyl-tridecyl)-chroman-5-ylmethylsulfanyl]-2-methyl-propionyl}-pyrrolidine-2-carboxylic acid;
2-(2,2-Dichloro-vinyl)-2,5,7,8-tetramethyl-chroman-6-ol;
2-(2,2-Dibromo-vinyl)-2,5,7,8-tetramethyl-chroman-6-ol;
5-(5-Chloro-3-methyl-pent-2-enyl)-2,2,7,8-tetramethyl-chroman-6-ol;
5-Chloro-2-(2,5-dimethyl-thiophen-3-yl)-2,7,8-trimethyl-chroman-6-ol;
2-(3-Chloro-propyl)-5,7-dimethyl-2-thiophen-2-yl-chroman-6-ol;
5-Chloro-2-(2,5-dimethyl-thiazol-4-yl)-2,7,8-trimethyl-chroman-6-ol;
5-Chloro-2-(2,5-dimethyl-thiazol-4-yl)-2,7,8-trimethyl-2H-chromen-6-ol; and
5-Chloro-2-(2,5-dimethyl-thiazol-4-yl)-2,7,8-trimethyl-chroman-6-ol.

Another aspect of this invention is the processes for preparing compounds of Formula I and is set forth in "Description of the Invention".

Certain embodiments of the invention provide novel and preferred combinations of substituent groups pendant from the formulae of the different inventions

DETAILED DESCRIPTION OF THE INVENTION

Definitions

As used in the present specification, the following words and phrases are generally intended to have the meanings as set forth below, except to the extent that the context in which they are used indicates otherwise.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl," as defined below.

It will be understood by those skilled in the art with respect to any group containing one or more substituents that such groups are not intended to introduce any substitution or substitution patterns that are sterically impractical and/or physically non-feasible.

The term "acyl" refers to the groups —C(O)—H, —C(O)-(optionally substituted alkyl), —C(O)-(optionally substituted cycloalkyl), —C(O)-(optionally substituted alkenyl), —C(O)-(optionally substituted cycloalkenyl), —C(O)-(optionally substituted aryl), and —C(O)-(optionally substituted heterocyclyl).

The term "alkenyl" refers to a monoradical branched or unbranched, unsaturated or polyunsaturated hydrocarbon chain, having from about 2 to 20 carbon atoms, more preferably about 2 to 10 carbon atoms. This term is exemplified by groups such as ethenyl, but-2-enyl, 3-methyl-but-2-enyl (also referred to as "prenyl", octa-2,6-dienyl, 3,7-dimethyl-octa-2,6-dienyl (also referred to as "geranyl"), and the like.

The term "acyloxy" refers to the moiety —O-acyl, including, for example, —O—C(O)-alkyl.

The term "alkoxy" refers to the groups —O-alkyl, —O-alkenyl, —O-cycloalkyl, —O-cycloalkenyl, and —O-alkynyl. Preferred alkoxy groups are —O-alkyl and include, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

The term "substituted alkoxy" refers to the groups —O-(substituted alkyl), —O-(substituted alkenyl), —O-(substituted cycloalkyl), —O-(substituted cycloalkenyl), —O-(substituted alkynyl) and —O-(optionally substituted alkylene)-alkoxy.

The term "alkyl" refers to a monoradical branched or unbranched saturated hydrocarbon chain preferably having from about 1 to 20 carbon atoms, more preferably about 1 to 10 carbon atoms, and even more preferably about 1 to 6 carbon atoms. The term "alkyl" also means a combination of linear or branched and cyclic saturated hydrocarbon radical consisting solely of carbon and hydrogen atoms. This term is exemplified by groups such as methyl, ethyl, n-propyl, iso-propyl, n-butyl, iso-butyl, n-hexyl, n-decyl, tetradecyl, and the like. The term "lower alkyl" refers to a monoradical branched or unbranched saturated hydrocarbon chain of 1 to 6 atoms.

The term "substituted alkyl" refers to an alkyl group in which 1 or more (up to about 5, preferably up to about 3) hydrogen atoms is replaced by a substituent independently selected from the group: =O, =S, acyl, acyloxy, optionally substituted alkoxy, optionally substituted amino (wherein the amino group may be a cyclic amine), azido, carboxyl, (optionally substituted alkoxy)carbonyl, (optionally substituted amino)carbonyl, cyano, optionally substituted cycloalkyl, optionally substituted cycloalkenyl, halogen, hydroxyl, nitro, sulfamoyl, sulfanyl, sulfinyl, sulfonyl, and sulfonic acid. One of the preferred optional substituents for alkyl is hydroxy, exemplified by hydroxyalkyl groups, such as 2-hydroxyethyl, 3-hydroxypropyl, 3-hydroxybutyl, 4-hydroxybutyl, and the like; dihydroxyalkyl groups (glycols); such as 2,3-dihydroxypropyl, 3,4-dihydroxybutyl, 2,4-dihydroxybutyl, and the like; aminoalkyl groups such as dimethyl aminoalkyl, piperidinylalkyl, morpholinylalkyl, and those compounds known as polyethylene glycols, polypropylene glycols and polybutylene glycols, and the like. Another preferred optional substituent for alkyl is sulfanyl exemplified by allylsulfanyl, carboxypropylsulfanyl, 2-methyl-propionyl-pyrrolidine-2-carboxylic acid, 5-methyl-1-H-benzimidazol-2-yl-sulfanyl, sulfoxyethylsulfanyl, 4,6-dimethyl-pyrimidin-2-ylsulfanyl, 4 carboxy-benzyl-sulfanyl, isobutylsulfanyl, and the like. Other preferred optional substituents for alkyl are —N-hydroxyureidyl, —N-hydroxythioureidyl or —N-hydroxyacetamide.

The term "alkylene" refers to a diradical derived from the above-defined monoradical, alkyl. This term is exemplified by groups such as methylene (—CH$_2$—), ethylene (—CH$_2$CH$_2$—), the propylene isomers [e.g., —CH$_2$CH$_2$CH$_2$— and —CH(CH$_3$)CH$_2$—] and the like.

The term "substituted alkylene" refers to a diradical derived from the above-defined monoradical, substituted alkyl. Examples of substituted alkylenes are chloromethylene (—CH(Cl)—), aminoethylene (—CH(NH$_2$)CH$_2$—), methylaminoethylene (—CH(NHMe)CH$_2$—), 2-carboxypropylene isomers (—CH$_2$CH(CO$_2$H)CH$_2$—), ethoxyethylene (—CH$_2$CH$_2$O—CH$_2$CH$_2$—), ethyl(N-methyl)aminoethylene (—CH$_2$CH$_2$N(CH$_3$)CH$_2$CH$_2$—), 1-ethoxy-2-(2-ethoxyethoxy)ethylene (—CH$_2$CH$_2$O—CH$_2$CH$_2$—OCH$_2$CH$_2$—OCH$_2$CH$_2$—), and the like.

The term "amino" refers to the group —NH$_2$ as well as to the groups —NHR or —NRR where each R is independently selected from the group: optionally substituted alkyl, optionally substituted cycloalkyl, optionally substituted alkenyl, optionally substituted cycloalkenyl, optionally substituted alkynyl, optionally substituted aryl, optionally substituted heterocyclyl, acyl, optionally substituted alkoxy, carboxy and alkoxycarbonyl, and where —NRR may be a cyclic amine.

The term "amino acid" or "natural amino acid" refers to any of the twenty (20) common amino acids as generally accepted in the peptide art.

The term "aromatic" refers to a cyclic or polycyclic moiety having a conjugated unsaturated (4n+2) π electron system (where n is a positive integer), sometimes referred to as a delocalized π electron system.

The term "aryl" refers to an aromatic cyclic hydrocarbon group of from 6 to 20 carbon atoms having a single ring (e.g., phenyl) or multiple condensed (fused) rings (e.g., naphthyl or anthryl). Preferred aryls include phenyl, naphthyl and the like.

The term "substituted aryl" refers to an aryl group as defined above, which unless otherwise constrained by the definition for the aryl substituent, is substituted with from 1 to 5 substituents, and preferably 1 to 3 substituents, independently selected from the group consisting of: hydroxy, thiol, acyl, acyloxy, optionally substituted alkenyl, optionally substituted alkoxy, optionally substituted alkyl (such as tri-halomethyl), optionally substituted alkynyl, optionally substituted amino, optionally substituted aryl, optionally substituted aryloxy, azido, carboxyl, (optionally substituted alkoxy)carbonyl, (optionally substituted amino)carbonyl, cyano, optionally substituted cycloalkyl, optionally substituted cycloalkenyl, halogen, optionally substituted heterocyclyl, optionally substituted heterocyclooxy, hydroxyl, nitro, sulfanyl, sulfinyl, sulfanyl, and sulfonic acid. Preferred aryl substituents include alkyl, alkenyl, alkoxy, halo, cyano, nitro, trihalomethyl, carboxy, amino, amido, sulfonamido, and sulfinyl.

The term "carbonyl" refers to the di-radical "—C(=O)—", which is also illustrated as "—C(O)—".

The term "(optionally substituted alkoxy)carbonyl" refers to the groups: —C(O)O-(optionally substituted alkyl), —C(O)O-(optionally substituted cycloalkyl), —C(O)O-(optionally substituted alkenyl), and —C(O)O-(optionally substituted alkynyl). These moieties are also referred to as esters.

The term "(optionally substituted amino)carbonyl" refers to the group —C(O)-(optionally substituted amino). This moiety is also referred to as a primary, secondary or tertiary carboxamide.

The term "carboxy" or "carboxyl" refers to the moiety "—C(O)OH", which is also illustrated as "—COOH".

The term "cognitive disorders" refers to disorders generally characterized by symptoms of forgetfulness, confusion, memory loss, impairment in attention and memory, behavioral and relation disorders, abulia, lack of interest, affective disturbances, and/or, in some cases poor personal care. These symptoms may arise as a result of the general aging process and/or from organic brain disease, cerebrovascular disease, head injury, or developmental or genetic defects. Cognitive disorders include Alzheimer's disease, senile dementia, anxiety, HIV-related dementia, diabetic neuropathies; depression; Parkinson's disease; drug dependency; substance abuse; consciousness disorders, sleeping disorders, disorders of the circadian rhythm, mood disorders, epilepsy; Down's syndrome; Huntington's chorea or disease; stress-related somatic disorders; Creutzfeldt-Jacob disease; disorders associated with panic, phobia or stress.

The term "cycloalkyl" refers to non-aromatic cyclic hydrocarbon groups of having about 3 to 40 (preferably about 4 to 15) carbon atoms having a single ring or multiple condensed or bridged rings. Such cycloalkyl groups include, by way of example, single ring structures such as cyclopropyl, cyclobutyl, cyclopentyl, cyclooctyl, and the like, or multiple ring structures such as adamantanyl, and the like. The term "cycloalkyl" additionally encompasses spiro systems wherein the cycloalkyl ring has a carbon ring atom in common with another ring.

The term "substituted cycloalkyl" refers to a cycloalkyl group substituted with from 1 to 5 substituents, and preferably 1 to 3 substituents, independently selected from the group consisting of: =O, =S, acyl, acyloxy, optionally substituted alkenyl, optionally substituted alkoxy, optionally substituted alkyl (such as tri-halomethyl), optionally substituted alkynyl, optionally substituted amino, optionally substituted aryl, optionally substituted aryloxy, azido, carboxyl, (optionally substituted alkoxy)carbonyl, (optionally substituted amino)carbonyl, cyano, optionally substituted cycloalkyl, optionally substituted cycloalkenyl, halogen, optionally substituted heterocyclyl, optionally substituted heterocyclooxy, hydroxyl, nitro, sulfanyl, sulfinyl, sulfanyl, and sulfonic acid. A cycloalkyl ring substituted with an alkyl group is also referred as "alkylcycloalkyl".

The term "halo" or "halogen" refers to fluoro, chloro, bromo and iodo.

The terms "heterocycle", "heterocyclic", "heterocyclo", and "heterocyclyl" refer to a monovalent, saturated, partially unsaturated or unsaturated (aromatic), carbocyclic radical having one or more rings incorporating one, two, three or four heteroatoms within the ring (chosen from nitrogen, oxygen, and/or sulfur). Preferred heterocycles include morpholine, piperidine, piperazine, thiazole, thiazolidine, isothiazole, oxazole, isoxazole, pyrazole, pyrazolidine, pyrazoline, imidazole, imidazolidine, benzothiazole, pyridine, pyrazine, pyrimidine, pyridazine, pyrrole, pyrrolidine, quinoline, quinazoline, purine, carbazole, benzimidazole, pyrimidine, thiophene, benzothiophene, pyran, tetrahydropyran, benzopyran, furan, tetrahydrofuran, indole, indoline, indazole, xanthene, thioxanthene, acridine, quinuclidine, and the like.

The terms "substituted heterocycle", "substituted heterocyclic", "substituted heterocyclo" and "substituted heterocyclyl" refer to a heterocycle group as defined above, which unless otherwise constrained by the definition for the heterocycle, is substituted with from 1 to 5 substituents, and preferably 1 to 3 substituents, independently selected from the group consisting of: hydroxy, thiol, acyl, acyloxy, optionally substituted alkenyl, optionally substituted alkoxy, optionally substituted alkyl (such as tri-halomethyl), optionally substituted alkynyl, optionally substituted amino, optionally substituted aryl, optionally substituted aryloxy, azido, carboxyl, (optionally substituted alkoxy)carbonyl, (optionally substituted amino)carbonyl, cyano, optionally substituted cycloalkyl, optionally substituted cycloalkenyl, halogen, optionally substituted heterocyclyl, optionally substituted heterocyclooxy, hydroxyl, nitro, sulfanyl, sulfinyl, and sulfonic acid. Preferred substituted heterocycles include thiazolidine-2,4-dione and 3-methyl-5-oxo-4,5-dihydro-1H-pyrazol.

The term "inflammation", "inflammatory conditions", or "inflammation conditions" includes but is not limited to muscle fatigue, osteoarthritis, rheumatoid arthritis, inflammatory bowel syndrome or disorder, skin inflammation, such as atopic dermatitis, contact dermatitis, allergic dermatitis, xerosis, eczema, rosacea, seborrhea, psoriasis, atherosclerosis, thermal and radiation burns, acne, oily skin, wrinkles, excessive cellulite, excessive pore size, intrinsic skin aging, photo aging, photo damage, harmful UV damage, keratinization abnormalities, irritation including retinoid induced irritation, hirsutism, alopecia, dyspigmentation, inflammation due to wounds, scarring or stretch marks, loss of elasticity, skin atrophy and gingivitis.

The term "ischemia" refers to deficiency of blood to an organ or tissue due to functional constriction or actual obstruction of a blood vessel. Cerebral ischemia, also known as stroke, usually results from the interruption or reduction of blood and oxygen to the blood vessels of the brain; more rarely this may be the result of a hemorrhage. Signs of stroke include paralysis, slurred speech, general confusion, impairment of gait, cortical sensory loss over toes, foot and leg, and urinary incontinence, to name just a few. Many types of heart disease including cardiac arrhythmias or diseases due to cardiac structural abnormalities may produce cerebral emboli. Atrial fibrillation from any cause, including rheumatic valvular disease, may result in emboli being produced which can migrate into the arteries of the brain. Emboli formation and migration can occur as a result of atherosclerotic cardiovascular disease and myocardial infarction. Emboli formation is also a definite risk for intracardiac surgery and prosthetic valve replacement. Heart bypass surgery and angioplasty can result in the formation of microemboli which can migrate into the arteries of the brain and cause a series of occlusions in a number of arteries, resulting in mental impairment. Cerebral embolism is also the principal complication in the transplant of artificial hearts. Furthermore, the overall risk of stroke after any type of general surgery is 0.2 to 1 percent. The vegetations of acute and subacute bacterial endocarditis can give rise to emboli which can occlude a major intracranial artery. Populations at risk of ischemia include but are not limited to patients scheduled for coronary arterial bypass graft surgery (CABG), patients at risk for postoperative complications, patients with subarachnoid hemorrhage (SAH), patients with a first or second ischemic stroke, patients with acute ischemic stroke, patients undergoing cardiopulmonary resuscitation (CPR), patients with temporary lobotomy, patients with dominant hemisphere resection, patients receiving prophylactic brain radiation, patients with closed head trauma with neurological loss, patients with microvascular multi-infarct dementia, patients with homozygous and heterozygous MELAS (Mitochondria) myopathy, encephalopathy, lactacidosis, stroke); patients with Myoclonic Epilepsy with Ragged Red Fibers (MERFF); patients with atherosclerotic or progressive supranuclear palsy disease, patients with symptomatic and asymptomatic Huntington's disease, patients with neonatal asphyxia, patients with meningitis or encephalitis, patients with post herpetic neuropathy, patients with intermittent claudication, patients with spinal cord injury, patients with Huntington's disease, Amyotrophic Lateral Sclerosis (ALS) or Friedreich's ataxia, patients with diabetic neuropathy or patients with a disease associated with a hypercoagulable state secondary to systemic disease, carcinoma, vasoconstriction (including reversible cerebral vasoconstriction, e.g. migraine, trauma, idiopathy), or venous conditions (including dehydration, pulmonary embolism, pericranial infection, postpartum and postoperative states and system cancer).

The term "isomers" or "stereoisomers" relates to compounds that have identical molecular formulae but that differ in the arrangement of their atoms in space. Stereoisomers that are not mirror images of one another are termed "diastereoisomers" and stereoisomers that are non-superimposable mirror images are termed "enantiomers", or sometimes optical isomers. A carbon atom bonded to four non-identical substituents is termed a "chiral center". Certain compounds of the present invention have one or more chiral centers and therefore may exist as either individual stereoisomers or as a mixture of stereoisomers. This invention includes all possible stereoisomers as individual stereoisomers or as a mixture of stereoisomers.

A "lipoxygenase-mediated condition" or a "disorder mediated by lipoxygenases" means any condition, disorder or disease related to or otherwise associated with a lipoxygenase enzyme or the inhibition thereof, including, by way of example and without limitation, diseases involving apoptosis in cancer cells such as prostatic cancer, gastric cancer, colorectal or esophageal cancer and airways carcinoma; diseases involving hypoxia, or anoxia such as atherosclerosis, myocardial infarction, cardiovascular disease, heart failure (including chronic and congestive heart failure), cerebral ischemia, retinal ischemia, myocardial ischemia, post surgical cognitive dysfunction and other ischemias; diseases involving inflammation, including diabetes, arterial inflammation, inflammatory bowel disease, renal disease, pre-menstrual syndrome, asthma, allergic rhinitis, gout; cardiopulmonary inflammation, rheumatoid arthritis, osteoarthritis, muscle fatigue and disorders of the skin such as acne; disorders of the airways such as asthma, chronic bronchitis, human airway carcinomas, mucus hypersecretion, chronic obstructive pulmonary disease (COPD) and adult respiratory distress syndrome; diseases involving neurodegeneration and neuroinflammation including Alzheimer's, dementia and Parkinson's disease; peripheral neuropathy including spinal chord injury, head injury and surgical trauma, and allograft tissue and organ transplant rejection; diseases involving the autoimmune system such as psoriasis, eczema, rheumatoid arthritis, and diabetes; and disorders involving the bone loss or bone formation.

The term "mitochondrial diseases or disorders" of which hundreds of varieties have been identified, can cause a complex variety of symptoms. These include muscle weakness, muscle cramps, seizures, food reflux, learning disabilities, deafness, short stature, paralysis of eye muscles, diabetes, cardiac problems and stroke-like episodes, to name a few. The symptoms can range in severity from life-threatening to almost unnoticeable, sometimes taking both extremes in members of the same family. Because some people have specific subsets of these symptoms, clinical researchers have grouped those that occur together into "syndromes," producing a bewildering array of descriptive acronyms such as MELAS (mitochondrial encephalomyopathy with lactic acidosis and stroke-like episodes) or MERFF (myoclonus epilepsy with ragged red fibers). This term also includes disorders such as Kearns-Sayre syndrome (KSS), Leigh's syndrome, maternally inherited Leigh's syndrome (MILS), Myogastrointestinal encephalomyopathy (MNGIE), Neuropathy, ataxia and retinitis pigmentosa (NARP), Progressive external opthalmoplegia (PEO), and Pearson syndrome.

The term "neurodegenerative disorders" refers to disorders characterized by a loss of neurons and may or may not include a neuroinflammatory process. Neurodegenerative disorders include stroke, head trauma, cerebral hypoxia, spinal cord injury, senile dementia, Alzheimer's disease, amyotrophic lateral sclerosis (ALS) and other motor neuron diseases, cerebral amyloid angiopathy, HIV-related dementia, Parkinson's disease, Huntington's disease, prion diseases, myasthenia gravis, Down's syndrome, Creutzfeldt-Jakob disease, Friedreich's ataxia, Fergusson and Critchley's ataxia and other ataxias, Leber's hereditary optic neuropathy diabetic neuropathy, neuropathic pain, encephalitis, meningitis, and Duchenne's muscular dystrophy.

The term "neuroinflammation" or "neuroinflammatory diseases, disorders or conditions" refers to diseases, disorders or conditions characterized by large numbers of reactive microglia in postmortem brain samples, indicative of an active inflammatory process (McGeer E. G. and McGeer P. L., "Neurodegeneration and the immune system". Calne D. B., ed. Neurodegenerative Diseases, 1994:277-300). Neuroinflammation refers to inflammation which occurs in response to brain injury or autoimmune disorders, and has been shown to cause destruction of healthy neuronal and/or cerebral tissue. Neuroinflammation relates to mechanisms implicated in a broad range of acute and chronic neurodegenerative disorders, including stroke, head trauma, cerebral amyloid angiopathy, HIV-related dementia, Huntington's disease, prion diseases, meningitis, myelin degradation, epilepsy, Down's syndrome, post-ischemic brain injury, encephalopathy, Parkinson's disease, senile dementia, Alzheimer's disease, amyotrophic lateral sclerosis, multiple sclerosis and certain disorders involving the peripheral nervous system, such as myasthenia gravis and Duchenne's muscular dystrophy.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

The term "pharmaceutically acceptable salt" refers to salts which retain the biological effectiveness and properties of the compounds of this invention and which are not biologically or otherwise undesirable. In some cases, the compounds of this invention are capable of forming acid and/or base salts by virtue of the presence of amino and/or carboxyl groups or groups similar thereto. Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diary) amines, triaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heterocyclic, and the like. Also included are amines where the two or three substituents, together with the amino nitrogen, form a heterocyclic group.

Specific examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

The term "sulfanyl" refers to the groups: —S-(optionally substituted alkyl), —S-(optionally substituted aryl), —S-(optionally substituted heterocyclyl). Preferred sulfanyl groups include, by way of example, allylsulfanyl (—SCHCH$_2$=CH$_2$), n-(iso-butylsulfanyl) (—SCH$_2$CH(CH$_3$)$_2$), 3-thiazol-2-ylsulfanyl, captopril, 3-carboxy-2-methylpropylsulfanyl, and the like.

The term "sulfonic acid" refers to the group: —S(O$_2$)—OH.

The term "therapeutically effective amount" refers to that amount of a compound of this invention, that is sufficient to effect treatment, as defined below, when administered to a mammal in need of such treatment. The therapeutically effective amount will vary depending upon the subject and disease condition being treated, the weight and age of the subject, the severity of the disease condition, the particular compound chosen, the dosing regimen to be followed, timing of administration, the manner of administration and the like, all of which can readily be determined by one of ordinary skill in the art.

The term "treatment" or "treating" means any treatment of a disease or disorder in a mammal, including:

preventing or protecting against the disease or disorder, that is, causing the clinical symptoms not to develop;

inhibiting the disease or disorder, that is, arresting or suppressing the development of clinical symptoms; and/or relieving the disease or disorder that is, causing the regression of clinical symptoms.

It will be understood by those skilled in the art that in human medicine, it is not always possible to distinguish between "preventing" and "suppressing" since the ultimate inductive event or events may be unknown, latent, or the patient is not ascertained until well after the occurrence of the event or events. Therefore, as used herein the term "prophylaxis" is intended as an element of "treatment" to encompass both "preventing" and "suppressing" as defined herein. The term "protection," as used herein, is meant to include "prophylaxis."

Nomenclature

In general, the nomenclature used in this application was generated using or with the help of version 2.2 of the AUTONOM™ naming package within the ChemOffice® version 7.0.3 suite of programs by CambridgeSoft Corp (Cambridge, Mass.).

A compound of Formula I wherein -A-B— is —CH$_2$—CH$_2$, n is 3, R$^1$, R$^5$, and R$^6$ are methyl, R$^3$ and R$^4$ are hydrogen, R$^2$ is thiazolidine-2,4-dione, is named 5-[3-(6-hydroxy-2,7,8-trimethyl-chroman-2-yl)-propyl]-thiazolidine-2,4-dione.

Synthesis of the Compounds of the Invention

Synthetic Reaction Parameters

The terms "solvent", "inert organic solvent" or "inert solvent" mean a solvent inert under the conditions of the reaction being described in conjunction therewith. Solvents employed in synthesis of the compounds of the invention include, for example, methanol ("MeOH"), acetone, water, acetonitrile, 1,4-dioxane, dimethylformamide ("DMF"), benzene, toluene, tetrahydrofuran ("THF"), chloroform, methylene chloride (also named dichloromethane ("DCM"), diethyl ether, ethyl acetate ("EtOAc"), pyridine and the like, as well as mixtures thereof. Unless specified to the contrary, the solvents used in the reactions of the present invention are inert organic solvents.

The term "q.s." means adding a quantity sufficient to achieve a stated function, e.g., to bring a solution to the desired volume (i.e., 100%), and "MOM" refers to methoxymethyl.

Unless specified to the contrary, the reactions described herein take place at atmospheric pressure within a temperature range from 0° C. to 110° C. (preferably from 0° C. to 25° C.; most preferably at "room" or "ambient" temperature ("RT"), e.g., 20° C.). Further, unless otherwise specified, the reaction times and conditions are intended to be approximate, e.g., taking place at about atmospheric pressure within a temperature range of about 0° C. to about 110° C. (preferably from about 0° C. to about 25° C.; most preferably at about "room" or "ambient" temperature, e.g., approximately 20° C.) over a period of about 1 to about 10 hours (preferably about 5 hours).

Isolation and purification of the compounds and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples herein below. However, other equivalent separation or isolation procedures can also be used.

Reaction Scheme 1

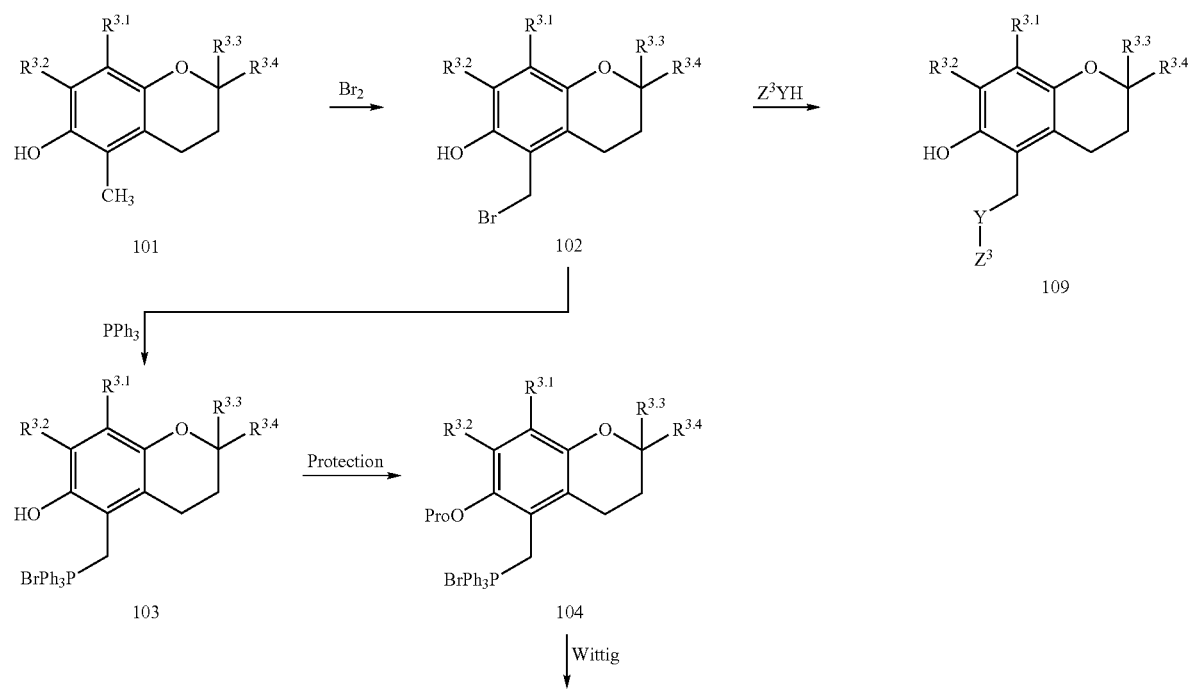

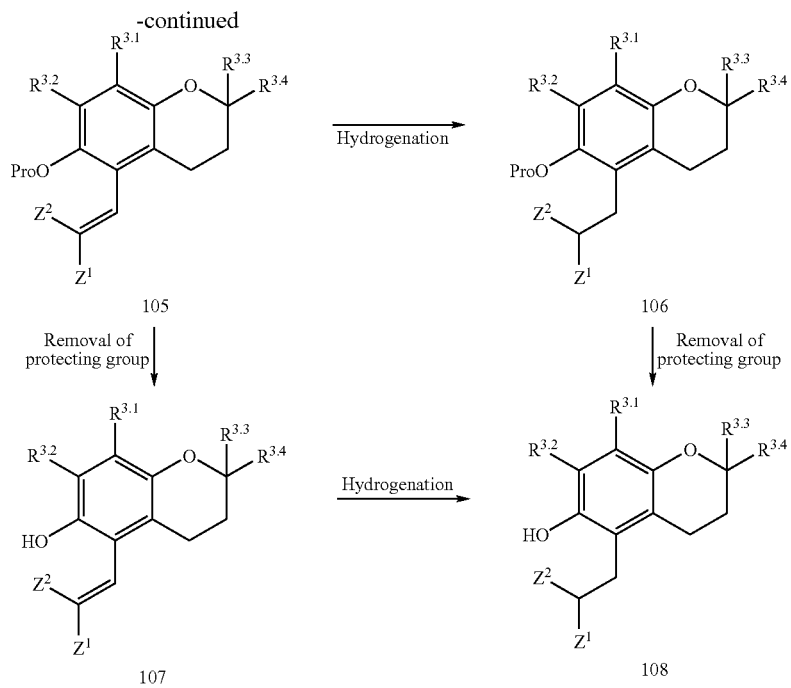

Compounds of Formula I wherein the 5-position is substituted with a substituted alkyl of at least two carbons or a substituted alkenyl, can be prepared following Scheme 1. In Scheme 1, $R^{3.3}$, $R^{3.4}$ are hydrocarbon groups, preferably unsubstituted alkyl groups, $R^{3.1}$ and $R^{3.2}$ are hydrocarbons. Pro is a protective group and $Z^1$ and $Z^2$ are the substituents of interest for the alkyl group at the 5 position, or $Z^1$ is hydrogen and $Z^2$ is the substituent of interest for the alkyl group.

The chroman of Formula 101 is brominated in an inert solvent to give the methylbromide derivative 102, which is then converted to the phosphonium salt of Formula 103 by addition of triphenylphosphine. The hydroxy group of the phosphonium salt derivative 103, can be protected with for example, the methoxymethyl (MOM) group by reaction with chloromethylmethyl ether to give a MOM-protected compound of Formula 104. In the next step a Wittig reaction is performed with an aldehyde or a ketone of formula $Z^1Z^2C$(O), in an inert solvent in the presence of a strong base, such as sodium alkoxide or sodium hydride, preferably sodium hydride to give a compound of Formula 105. Hydrogenation of the double bond of compound of Formula 105 in a hydrogen atmosphere in the presence of a catalyst such as Palladium on charcoal can yield compound of Formula 106, which after removal of the protective group can give the desired saturated compound of Formula 108. Removal of the protecting group can be effected with an acid such as hydrochloric acid in a solvent such as an alcohol, preferably in methanol. Deprotection of compound of Formula 105 with an acid can give the unsaturated compound of Formula 107, which if desired, can also be hydrogenated to give the compound of Formula 108, under the conditions described herein.

Alternatively, the chromans of Formula 101, wherein $R^{3.3}$ and $R^{3.4}$ have respectively the meaning of $R^1$ and $(CH_2)_n.R^2$ of Formula I, and further wherein $R^{3.1}$ and $R^{3.2}$ have the meaning of $R^5$ and $R^6$ of Formula I can be brominated as described herein to give a bromide derivative of Formula 102, which followed by the treatment with a compound of Formula $Z^3YH$ wherein Y is oxygen, sulfur or nitrogen and $Z^3$ is the desired substituent, in the presence of a mild base such as sodium or potassium carbonate, sodium or potassium bicarbonate, in an inert solvent, preferably methylene chloride, can give a compound of Formula 109.

Preferred Compounds

The compounds of Formula I encompass the chroman derivatives of the invention as disclosed, and/or the pharmaceutically acceptable salts of such compounds. In addition, the compounds of this invention include the individual stereochemical isomers and mixtures thereof, arising from the selection of substituent groups. It will be understood by those skilled in the art with respect to any group containing one or more substituents that such groups are not intended to introduce any substitution or substitution patterns that are sterically impractical and/or synthetically non-feasible.

Preferred for the compounds, pharmaceutical formulations, methods of manufacture and use of the present invention are the following combinations and permutations of substituent groups of Formula I.

Utility, Testing and Administration

General Utility

Without subscribing to a particular theory or mechanism of action, compounds of the invention may target certain enzymes known as "oxidoreductases" that function widely across a variety of physiological processes, more particularly certain compounds of the present invention may target lipoxygenases such as 5-lipoxygenase, 15-lipoxygenase, and/or 12/15-lipoxygenase. In particular, oxidoreductases catalyze reactions in which two molecules interact so that one molecule is oxidized and the other is reduced. Alterations in oxidoreductases are thought to account for as many as 3% of all known human genetic diseases. Abnormalities in oxidoreductase activity may underlie such disorders as congestive heart failure, respiratory chain defects (e.g., abnormalities associated with enzymes of the respiratory chain, acute respiratory distress syndrome (ARDS)), glycogen storage disease, end-stage renal disease, and rheumatoid arthritis. Inhibitors of lipoxygenases are known to be useful in the prevention or treatment of, for example, disorders selected from apoptosis in cancer cells including prostatic cancer, gastric cancer, colorectal or esophageal cancer and airways carcinoma; diseases involving hypoxia, or anoxia including atherosclerosis, myocardial infarction, cardiovascular disease, heart failure (including chronic and congestive heart failure), cerebral ischemia, retinal ischemia, myocardial ischemia, post surgical cognitive dysfunction and other ischemias; diseases involving inflammation, including diabetes, arterial inflammation, inflammatory bowel disease, renal disease, pre-menstrual syndrome, asthma, allergic rhinitis, gout; cardiopulmonary inflammation, rheumatoid arthritis, osteoarthritis, muscle fatigue and disorders of the skin such as acne; disorders of the airways including asthma, chronic bronchitis, human airway carcinomas, mucus hypersecretion, chronic obstructive pulmonary disease (COPD) and adult respiratory distress syndrome; diseases involving neurodegeneration and neuroinflammation including Alzheimer's, dementia and Parkinson's disease; peripheral neuropathy including spinal chord injury, head injury and surgical trauma, and allograft tissue and organ transplant rejection; diseases involving the autoimmune system including psoriasis, eczema, rheumatoid arthritis, and diabetes; and disorders involving the bone loss or bone formation It has surprisingly been found that certain compounds limit or prevent damage to organelles, cells, and tissues caused by mitochondria) dysfunction, oxidative stress or neuroinflammation, as demonstrated by providing protection in standard experimental models of mitochondrial dysfunction caused by MPP+ and MPTP (1-methyl-4-phenylpyridinium and 1-methyl-4-phenyl-1,2,3,4-tetrahydropyridine), of oxidative stress caused by beta amyloid or high glutamate or of neuroinflammation caused by LPS and Interferon-gamma. Certain compounds also show protection in an experimental model using FRDA fibroblasts and may be used for the treatment of Friedreich's Ataxia and other ataxias, Leber's hereditary optic neuropathy (LHON), mitochondrial myopathy, encephalopathy, lactacidosis, stroke (MELAS), Myoclonic Epilepsy with Ragged Red Fibers (MERFF), macular degeneration, Down's syndrome, Creutzfeldt-Jakob syndrome.

Compound, compositions, formulations, and methods of the present invention are useful for the treatment of disorders characterized by neuroinflammation, neurodegeneration, defective mitochondrial activity, oxidative stress and inflammation. In particular, compounds of the present invention can be used in the treatment of diseases such as degenerative diseases of the brain ((Wernicke-Korsakoff disease, Kreuzfeldt-Jakob disease (KJD), Hallervorden-Spatz disease, Schilder's disease, Alzheimer's disease, senile dementia, Down's syndrome in middle age, Abercrombie's disease, Prion diseases, Zellweger syndrome, Alper's Syndrome), spinocerebellar degenerations (spinal ataxia, cerebellar cortical degenerations, Friedreich's ataxia and other ataxias), multiple system degenerations (Menzel, Dejerine-Thomas, Shy-Drager, and Machado Joseph), systemic disorders (Refsum disease, ataxia telangiectasia), epilepsy, mitochondrial disorders (MELAS, MERFF, KSS, Leigh's, MILS, MNGIE, NARP, PEO, Pearson), demyelinating core disorders (multiple sclerosis, acute transverse myelitis), muscular atrophies (amyotrophic lateral sclerosis (ALS), multiple sclerosis (MS), infantile spinal muscular atrophy, Huntington's disease, spinobulbar atrophy (SBA), juvenile spinal muscular atrophy, myasthenia gravis and other motor neuron diseases), movement disorder (drug-induced Parkinsonism or Parkinson's disease), retinopathy (Leber's hereditary optic neuropathy, age-related macular degeneration (AMD), cataracts), cerebral ischemia ("stroke" most often caused by thrombosis, vasoconstriction and embolism), myocardial ischemia (including chronic stable angina, angina pectoris, unstable angina and Prinzmetal's angina, silent ischemia, reinfarction, reocclusion, restenosis, myocardial infarction and other forms of heart disease), diabetes, renal disease, pre-menstrual syndrome (PMS), asthma, cardiopulmonary inflammatory disorders, chronic heart failure, rheumatoid arthritis, muscle fatigue, irritable bowel syndrome, inflammatory bowel disease, intermittent claudication and for the preservation of allograft tissue for transplantation. Certain compounds of the present invention are also useful in treating conditions falling with the group of dermatologic conditions, in particular prevention and protecting skin tissue against age-related damage or damage resulting from insults such as harmful ultraviolet (UV) radiation, stress and fatigue, and in the treatment of contact dermatitis, skin irritation, skin pigmentation, psoriasis, or acne.

Testing

This section describes how compositions incorporating compositions of the present invention are selected, using in vitro and/or in vivo models, and used as therapeutic interventions in the exemplary indications.

MPTP/MPP+-induced neurodegeneration of dopaminergic neurons is a well characterized model which is widely used to understand the pathogenesis of Parkinson's disease. The compounds were tested against MPTP/MPP+ induced neuronal death in vitro and in vivo as shown in the following examples. In vitro evaluation of protection against mitochondrial dysfunction was carried out using a substantia nigra-derived dopaminergic progenitor cell line (as described in Son J H, et al J W. (1999) *J Neurosci*, 19: 10-20), exposed to 1-methyl-4-phenylpyridinium (MPP+) In vivo evaluation was carried out using mice that had been treated with 1-methyl-4-phenyl-1,2,3,6-tetrahydropyridine (MPTP), a neurotoxin. MPTP is metabolized by astrocytes into 1-methyl-4-phenylpyridinium (MPP+), a substrate for the dopamine transporter which then selectively inhibits complex 1 of the mitochondrial electron transport chain. This results in depletion of ATP, the production of reactive oxygen species and, consequently cell death. In a number of species, including humans, non-primates and rodents, MPTP produces an irreversible and severe parkinsonian syndrome which includes virtually all the clinical features of the disease. The striking pathologic and clinical similarities between idiopathic Parkinson's disease and MPTP-induced Parkinsonism suggest that the two disorders share common pathogenic mechanism.

A cellular assay using FRDA-patient derived fibroblasts (as described by Jauslin, M L et al, *Human Molecular Genetics* 11; 3055-3063 (2002)); was used to determine the protective effects of the test compounds by analyzing survival of dermal fibroblasts taken from FRDA patients and unaffected normal donors under conditions of partial GSH depletion. Exposure of FRDA fibroblasts to BSO (L-buthionine (S,R)-sulfoximine) under conditions of restricted selenium causes depletion of cellular glutathione (GSH) and severe plasma membrane damage leading to cell death. Preincubation with the test compounds before the addition of BSO was used to determine if they could protect FRDA cells from BSO-mediated cell death.

In experiments carried out in support of the present invention according to methods detailed in the Examples, oxidative stress was induced on a neuronal cell line, and compounds were tested for their ability to prevent cell death. Using in vitro assays the potency and efficacy of test articles against redox injury and cell death can be established in a high throughput manner and the compounds found to have activity in those in vitro assays are then further tested in one or more animal models of cerebral ischemia ("stroke"), such as the middle cerebral artery occlusion (MCAO) model in rats.

Protection against redox stress can be evaluated in cell culture using high glutamate induced oxidative stress (HGOS) in mouse dopaminergic cell lines. The cytotoxic effect of glutamate is not due to excitotoxicity, as this cell line is devoid of inotropic glutamate receptors. Rather, the glutamate-induced toxicity of dopaminergic cells is associated with an inhibition of cystine transport which subsequently leads to depletion of intracellular glutathione (GSH) levels (Murphy T. H., et al. *Neuron* 2, 1547-1558, 1989), activation of neuronal 12-lipoxygenase (Li, Y. et al., *Neuron* 19, 453-463, 1997), increased ROS production (Tan S. et al., *J. Cell Biol.* 141, 1423-1432, 1998) and elevated intracellular $Ca^{2+}$ (Li, Y. et al., see supra). Some molecules were measured for their ability to protect cells against glutamate-induced stress and the assay is detailed in Examples.

Further validation of neuroantiinflammatory activity of compounds can be assessed in vitro by the inhibition of IL-1.beta. release from a microglial cell line.

Interleukin-1 (IL-1) is a proinflammatory cytokine that exists in two separate forms that share 30% sequence homology (alpha and beta). Constitutive expression of IL-1 is low in the brain but levels of both forms of this cytokine increase dramatically after injury. There is substantial evidence that IL-1 is an important mediator of neurodegeneration induced by cerebral ischemia (Touzani O et al, *J Neuroimmunol.*, 100:203-215, (1999)). Both IL-1 forms are rapidly induced in experimental models of stroke and administration of recombinant IL-1 beta enhances ischemic injury (see Hill J K. et al. *Brain Res.* 820:45-54, (1999), Hillhouse E W et al. *Neurosci Lett* 249:177-179, (1998), Loddick S A et al *J Cereb Blood Flow Metab* 16:932-940, (1996), Stroemer R P et al., *J Cereb Blood Flow Metab.* 18:833-839, (1998)). Conversely, blocking IL-1 actions with a receptor antagonist or a neutralizing antibody markedly reduces neuronal death and inflammation in models of ischemic damage (see Betz A L, *J Cereb Blood Flow Metab* 15:547-551, (1995); Relton J K, *Brain Res Bull* 29:243-246, (1992); Yamasaki Y et al, *Stroke* 26:676-680, (1995)). Furthermore, mice with decreased IL-1.beta. production (caspase-1 knockouts) are significantly protected from ischemic injury (Schielke G P, et al. *J Cereb Blood Flow Metab* 18:180-185, (1998)) and IL-1α and β double knockouts exhibit dramatically reduced ischemic infarct volumes compared with wild-type mice (87% reduction in cortex) (Boutin H et al., *J Neurosci* 21:5528-5534, (2001)).

In addition to a role in ischemic damage, IL-1 elevation has been associated with many neurodegenerative diseases. There is increasing evidence for a role of IL-1 in Alzheimer's Disease (AD) (Mrak R E et al. *Neurobiol Aging* 22(6):903-908, (2001)). Elevated levels of IL-1β have been shown to surround amyloid plaques in the disease and recent genetic studies have indicated that a polymorphism in IL-1α is linked to an increased risk of AD (3-6 fold increase) (Griffin W S et al., *J Leukoc Biol* 72(2):233-238, (2002)). This polymorphism has also been correlated with rate of cognitive decline in AD patients (Murphy G M et al., *Neurology,* 56(11)1595-1597, (2001)). The risk of AD is increased even further when the polymorphism in IL-1.alpha. is found in combination with another polymorphism in IL-1β (see Griffin W S, supra), providing convincing evidence that these cytokines play an important role in the pathology of the disease.

This assay measures the release of IL-1β from a mouse microglial cell line following an inflammatory challenge with LPS and interferon-gamma. The ability of test articles to inhibit microglial cell activation and IL-1β release is determined by co-incubation of the test article with the inflammatory challenge.

Cerebral ischemic insults are modeled in animals by occluding vessels to, or within, the cranium (Molinari, G. F., 1986, in H. J. M. Barnett, et al., (Eds) *Stroke: Pathophysiology, Diagnosis and Management*, Vol. 1, Churchill Livingstone, N.Y.). The rat middle cerebral artery occlusion (MCAO) model is one of the most widely used techniques to induce transient focal cerebral ischemia approximating cerebral ischemic damage in humans, e.g., those who suffer from a stroke. The middle cerebral artery used as the ischemic trigger in this model is the most affected vessel in human stroke. The model also entails a period of reperfusion, which typically occurs in human stroke victims. MCAO involving a two-hour occlusion has been found to produce the maximum size of cortical infarction obtainable without increased mortality at twenty-four hours.

Further validation of efficacy in neuroprotection can be assessed in functional tests, such as the grip strength test or the rotorod test. Animals treated with compounds that show neuroprotection maintain their pre-MCAO grip strength values after MCAO, as compared to untreated animals, which showed a significant reduction in grip strength, indicating loss of sensorimotor function. Likewise, animals treated with compounds that show neuroprotection also maintained their pre-MCAO rotorod activity scores after MCAO, as compared to untreated animals, which showed a significant reduction in rotorod scores, indicating loss of sensorimotor function at higher brain levels.

In vivo evaluation of anti-inflammatory activity can be determined by well characterized assays measuring Carrageenan-Induced Paw Edema and by Mouse Ear Inflammatory Response to Topical Arachidonic Acid. (Gabor, M., Mouse Ear Inflammation Models and their Pharmacological Applications, 2000). Carrageenan-Induced Paw Edema is a model of inflammation, which causes time-dependent edema formation following carrageenan administration into the intraplantar surface of a rat paw. The application of arachidonic acid (AA) to the ears of mice produces immediate vasodilation and erythema, followed by the abrupt development of edema, which is maximal at 40 to 60 min. The onset of edema coincides with the extravasations of protein and leukocytes. After one hour the edema wanes rapidly and the inflammatory cells leave the tissue so that at 6 hours the ears have returned to near normal. These assays, as described in the Examples, measure a test compound's ability to treat these inflammatory processes via systemic and topical routes of administration.

The 5-lipoxygenase pathway is a major synthetic pathway relevant to human inflammatory disease. 5-lipoxygenase catalyses the two first steps in the oxygenation of arachidonic acid (a polyunsaturated 20-carbon fatty acid) to leukotrienes. Leukotrienes are known to be important mediators of inflammatory and allergic reactions. The first step in the synthesis of leukotrienes, which is catalyzed by 5-lipoxygenase, is the formation of 5-HPETE. The rearrangement of 5-HPETE to form the unstable $LTA_4$, the rate-limiting step in the synthesis of the leukotrienes, is also catalyzed by 5-lipoxygenase. $LTA_4$ is then converted to either $LTB_4$ or $LTC_4$. $LTC_4$ is rapidly metabolized to $LTD_4$ and then to $LTE_4$. $LTC_4$, $LTD_4$ and $LTE_4$ are collectively referred to as the cysteinyl (Cys) leukotrienes.

Biosynthesis of $LTB_4$, $C_4$, $D_4$ and $E_4$ occurs predominantly in leukocytes, in response to a variety of immunological stimuli. The primary target of $LTB_4$ is the leukocyte where it elicits enzyme release, chemotaxis, adherence, and aggregation in nM concentrations. $LTB_4$ modulates immune responses and participates in the host-defense against infections. Hence, $LTB_4$ is an important chemical mediator in the development and maintenance of inflammatory reactions and disease states.

In vitro evaluation of the ability of a composition to inhibit the enzymes 5-lipoxygenase, 15-lipoxygenase, or 12/15 lipoxygenase as described in Walidge, N. B. et al *Anal. Biochem.*, 231: 354-358 (1995) using a high throughput colorimetric method; as well as in vitro evaluation of inhibiting $LTB_4$ is described in Examples.

Administration

The compounds of the invention are administered at a therapeutically effective dosage, e.g., a dosage sufficient to provide treatment for the disease states previously described. Administration of the compounds of the invention or the pharmaceutically acceptable salts thereof can be via any of the accepted modes of administration for agents that serve similar utilities.

While human dosage levels have yet to be optimized for the compounds of the invention, generally, a daily dose is from about 0.01 to 10.0 mg/kg of body weight, preferably about 0.1 to 5.0 mg/kg of body weight, and most preferably about 0.3 to 1.0 mg/kg of body weight. Thus, for administration to a 70 kg person, the dosage range would be about 0.7 to 140 mg per day, preferably about 7.0 to 105 mg per day, and most preferably about 21 to 70 mg per day. The amount of active compound administered will, of course, be dependent on the subject and disease state being treated, the severity of the affliction, the manner and schedule of administration and the judgment of the prescribing physician.

In employing the compounds of this invention for treatment of the above conditions, any pharmaceutically acceptable mode of administration can be used. The compounds of this invention can be administered either alone or in combination with other pharmaceutically acceptable excipients, including solid, semi-solid, liquid or aerosol dosage forms, such as, for example, tablets, capsules, powders, liquids, suspensions, suppositories, aerosols or the like. The compounds of this invention can also be administered in sustained or controlled release dosage forms, including depot injections, osmotic pumps, pills, transdermal (including electrotransport) patches, and the like, for the prolonged administration of the compound at a predetermined rate, preferably in unit dosage forms suitable for single administration of precise dosages. The compositions will typically include a conventional pharmaceutical carrier or excipient and a compound of this invention or a pharmaceutically acceptable salt thereof. In addition, these compositions may include other medicinal agents, pharmaceutical agents, carriers, adjuvants, and the like, including, but not limited to anticoagulants, blood clot dissolvers, permeability enhancers and slow release formulations.

Generally, depending on the intended mode of administration, the pharmaceutically acceptable composition will contain about 0.1% to 90%, preferably about 0.5% to 50%, by weight of a compound or salt of Formulae II or III, the remainder being suitable pharmaceutical excipients, carriers, etc.

One preferred manner of administration for the conditions detailed above is oral, using a convenient daily dosage regimen which can be adjusted according to the degree of affliction. For such oral administration, a pharmaceutically acceptable, non-toxic composition is formed by the incorporation of any of the normally employed excipients, such as, for example, mannitol, lactose, starch, magnesium stearate, sodium saccharine, talcum, cellulose, sodium crosscarmellose, glucose, gelatin, sucrose, magnesium carbonate, and the like. Such compositions take the form of solutions, suspensions, tablets, dispersible tablets, pills, capsules, powders, sustained release formulations and the like.

Preferably the compositions will take the form of a pill or tablet and thus the composition will contain, along with the active ingredient, a diluent such as lactose, sucrose, dicalcium phosphate, or the like; a lubricant such as magnesium stearate or the like; and a binder such as starch, gum acacia, polyvinylpyrrolidine, gelatin, cellulose and derivatives thereof, and the like.

Liquid pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, sodium acetate, sodium citrate, cyclodextrine derivatives, sorbitan monolaurate, triethanolamine acetate, triethanolamine oleate, etc. Actual methods of preparing such dosage forms are known, or will be apparent, to those skilled in this art; for example, see *Remington's Pharmaceutical Sciences*, Mack Publishing Company, Easton, Pa., 15th Edition, 1975. The composition or formulation to be administered will, in any event, contain a quantity of the active compound in an amount effective to alleviate the symptoms of the subject being treated.

Dosage forms or compositions containing active ingredient in the range of 0.005% to 95% with the balance made up from non-toxic carrier may be prepared.

For oral administration, a pharmaceutically acceptable non-toxic composition is formed by the incorporation of any of the normally employed excipients, such as, for example pharmaceutical grades of mannitol, lactose, starch, magnesium stearate, talcum, cellulose derivatives, sodium crosscarmellose, glucose, sucrose, magnesium carbonate, sodium saccharin, talcum and the like. Such compositions take the form of solutions, suspensions, tablets, capsules, powders, sustained release formulations and the like. Such compositions may contain 0.01%-95% active ingredient, preferably 0.1-50%.

For a solid dosage form, the solution or suspension, in for example propylene carbonate, vegetable oils or triglycerides, is preferably encapsulated in a gelatin capsule. Such diester solutions, and the preparation and encapsulation thereof, are disclosed in U.S. Pat. Nos. 4,328,245; 4,409,239; and 4,410,545. For a liquid dosage form, the solution, e.g. in a polyethylene glycol, may be diluted with a sufficient quantity of a pharmaceutically acceptable liquid carrier, e.g. water, to be easily measured for administration.

Alternatively, liquid or semi-solid oral formulations may be prepared by dissolving or dispersing the active compound or salt in vegetable oils, glycols, triglycerides, propylene glycol esters (e.g. propylene carbonate) and the like, and encapsulating these solutions or suspensions in hard or soft gelatin capsule shells.

Other useful formulations include those set forth in U.S. Pat. Nos. Re. 28,819 and 4,358,603.

The formulation can be administered in a single unit dosage form for continuous treatment or in a single unit dosage form ad libitum when relief of symptoms is specifically required. For example, the formulation may be administered as a bolus or as a continuous intravenous infusion after onset of symptoms of stroke, myocardial infarction or chronic heart failure.

Another preferred manner of administration is the topical administration. "Topical administration" refers to application of the present compositions by spreading, spraying, etc. onto the surface of the skin. The typical amount applied may vary from about 0.1 mg of composition per square centimeter of skin to about 25 mg of composition per square centimeter of skin. Certain compounds of the present invention may be formulated for topical administration to the epidermis as ointments, creams or lotions or as transdermal patch. Formulations suitable for topical administration in the mouth include lozenges, pastilles and mouthwashes.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents, solubility enhancers, and the like, such as for example, sodium acetate, sorbitan monolaurate, triethanolamine oleate, cyclodextrins, etc.

A more recently devised approach for parenteral administration employs the implantation of a slow-release or sustained-release system, such that a constant level of dosage is maintained. See, e.g., U.S. Pat. No. 3,710,795. The percentage of active compound contained in such parenteral compositions is highly dependent on the specific nature thereof, as well as the activity of the compound and the needs of the subject. However, percentages of active ingredient of 0.01% to 10% in solution are employable, and will be higher if the composition is a solid which will be subsequently diluted to the above percentages. Preferably the composition will comprise 0.2-2% of the active agent in solution.

Nasal solutions of the active compound alone or in combination with other pharmaceutically acceptable excipients can also be administered.

Formulations of the active compound or a salt may also be administered to the respiratory tract as an aerosol or solution for a nebulizer, or as a microfine powder for insufflation, alone or in combination with an inert carrier such as lactose. In such a case, the particles of the formulation have diameters of less than 50 microns, preferably less than 10 microns.

EXAMPLES

The following preparations and examples are given to enable those skilled in the art to more clearly understand and to practice the present invention. They should not be considered as limiting the scope of the invention, but merely as being illustrative and representative thereof.

General Characterization Methods

As reported in the following examples, Nuclear Magnetic Resonance (NMR) spectra were recorded on a Bruker DTX 300 spectrometer using, in most cases, tetramethyl silane (TMS) as the internal reference. Mass spectra were obtained on an Agilent 1100 LC/MSD instrument using either electrospray ionization (positive or negative mode) (ESI) or atmospheric pressure chemical ionization (positive or negative mode) (APCI).

Example 1

2,2,7,8-Tetramethyl-4H-benzo[1,3]dioxin-6-ol

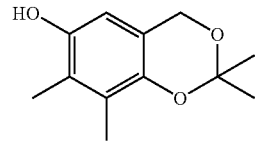

Step 1

To a mixture of 2,3-dimethylhydroquinone (1.38 g, 10 mmol), $K_2CO_3$ (2.76 g, 20 mmol), potassium iodide (0.83 g, 5 mmol) in 50 mL dry acetone was added benzyl bromide (1.88 g, 11 mmol). The resulting suspension was vigorously stirred for 48 at RT. The solid was filtered off and the liquid was concentrated. The residue was chromatographed to afford the benzyl derivative, 4-benzyloxy-3-methyl-phenol, as a light brown solid (1.15 g). $^1$H-NMR (300 MHz, $CDCl_3$) δ (ppm): 7.49-7.35 (m, 5H), 6.70 (d, J=8.7, 1H), 6.61 (d, J=8.7, 1H), 5.03 (s, 2H), 4.43 (s, 1H), 2.26 (s, 3H), 2.22 (s, 3H); MS (ESI) m/z: 229 (M+H$^+$, 100%).

Step 2:

To 684 mg (3 mmol) of 4-benzyloxy-3-methyl-phenol in 10 mL toluene and 1.5 mL DME (dimethoxyethane) in a sealable tube was added paraformaldehyde (1.8 g, 60 mmol). The tube was flushed with argon and sealed. It was heated to 130° C. for 48 h under stirring. After cooling to room temperature, the solid was filtered off and washed with 1:1 hexane/EtOAc and the liquid was concentrated. The residue was chromatographed to afford 4-benzyloxy-6-hydroxymethyl-2,3-dimethyl-phenol, as a light brown solid (640 mg). $^1$H-NMR (300 MHz, $CDCl_3/CD_3OD$)) δ (ppm): 7.43-7.29 (m, 5H), 6.55 (s, 1H), 4.95 (s, 2H), 4.70 (s, 2H), 2.18 (s, 3H), 2.16 (s, 3H); MS (ESI) m/z: 241 (M-OH$^-$, 100%).

Step 3:

A solution of 4-benzyloxy-6-hydroxymethyl-2,3-dimethyl-phenol (86 mg, 0.33 mmol) in dimethoxypropane (10 mL) in the presence of toluene sulfonic acid (7 mg) was stirred at RT for 15 h. It was added 30 mg of anion-exchange resin and stirring was continued for 20 more min. The resin was then filtered off and the solution was concentrated. The crude product was purified on silicagel column chromatography to afford 6-benzyloxy-2,2,7,8-tetramethyl-4H-benzo[1,3]dioxine as a white sticky solid (86 mg). $^1$H-NMR ($CDCl_3$, 300 MHz) δ (ppm): 7.51-7.35 (m, 5H), 6.45 (s, 1H), 5.02 (s, 2H), 4.85 (s, 2H), 2.26 (s, 3H), 2.19 (s, 3H), 1.59 (s, 6H); $^{13}$C-NMR δ (ppm): 150.6, 143.3, 137.8, 128.5, 127.8, 126.3, 125.8, 115.9, 105.4, 99.1, 70.9, 61.1, 24.9, 12.2, 11.5.

Step 4

To a solution of 6-benzyloxy-2,2,7,8-tetramethyl-4H-benzo[1,3]dioxine (86 mg, 0.29 mmol) in 10 mL EtOH was added Pd/C (15 mg, 10%). It was stirred in a hydrogen atmosphere for 1.5 h and filtered. The solution was concentrated and the crude product was purified on silicagel column chromatography to afford 2,2,7,8-tetramethyl-4H-benzo[1,3]dioxin-6-ol as a white solid (54 mg). $^1$H-NMR ($CDCl_3$, 300 MHz) δ (ppm): 6.28 (s, 1H), 4.77 (s, 1H), 4.76 (s, 2 H), 2.17 (s, 3H), 2.13 (s, 1H), 1.55 (s, 3H), 1.54 (s, 3H); $^{13}$C-NMR δ (ppm): 147.1, 142.9, 126.1, 122.7, 116.6, 107.5, 99.1, 60.9, 24.8, 11.9, 11.5.

Example 2

3-(6-Hydroxy-2,7,8-trimethyl-4H-benzo[1,3]dioxin-2-yl)-propionic Acid Ethyl Ester

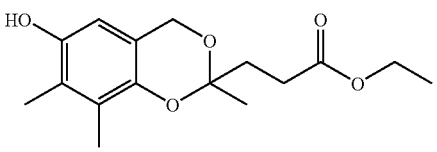

Step 1:

To 2 g of ethyl levulinate (13.9 mmol) in 2 mL of MeOH and 20 mL of trimethyl orthoformate was added 20 mL of toluenesulfonic acid. The mixture was stirred for 49 h followed by addition of 200 mg of basic ion-exchange resin and stirred for another 30 min. Solid was removed by filtration and the solution was concentrated and dried under high vacuum for 12 h. NMR indicated the full conversion to 4,4-dimethoxy-pentanoic acid ethyl ester.

Step 2:

To a solution of 4-benzyloxy-6-hydroxymethyl-2,3-dimethyl-phenol (52 mg, 0.20 mmol), prepared as in Example 29, in 0.5 mL of dry DMF was added the above dimethyl ketal, 4,4-dimethoxy-pentanoic acid ethyl ester (420 mg, 2.2 mmol) and 5 mg of pyridinium p-toluene sulfonate (PPTS). The mixture was stirred for 48 h and concentrated. The crude product was purified on silica gel column chromatography (8:1 hexane/EtOAc) to afford a clear oil containing the desired product and starting ketal material. This mixture was then dissolved in EtOH (5 mL) and hydrogenated in the presence of 10 mg of Pd/C for 1.5 h at atmosphere pressure. After filtration the solution was concentrated and purified by chromatography (5:1 hexane/EtOAc) to afford 3-(6-hydroxy-2,7,8-trimethyl-4H-benzo[1,3]dioxin-2-yl)-propionic acid ethyl ester as a light brown sticky oil (38 mg). $^1$H-NMR (300 MHz, CDCl$_3$) δ (ppm): 6.29 (s, 1H), 4.77 (s, 1H), 4.72 (q, J=14.9, 2H), 4.13 (q, J=7.2, 2H), 2.57-2.52 (m, 2H), 2.22-2.16 (m, 2H), 2.16 (s, 3H), 2.10 (s, 3H), 1.47 (s, 3H), 1.27 (t, J=7.2, 3H); $^{13}$C-NMR δ (ppm): 173.8, 147.2, 142.5, 126.0, 122.8, 116.5, 107.5, 99.5, 60.5, 33.9, 28.6, 21.8, 14.2, 11.9, 11.5.

Example 3

2,2,7,8-Tetramethyl-5-(3-methyl-but-2-enyl)-chroman-6-ol

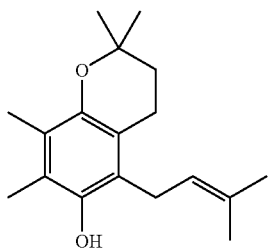

To a solution of 2,2,7,8-tetramethyl-chroman-6-ol (305 mg, 1.39 mmol), in 5 mL dry dioxane was added boron trifluoride (296 mg, 2.1 mmol). It was stirred for 3 min followed by dropwise addition of 2-methyl-but-3-en-2-ol solution (143 mg, 1.66 mmol, in 3 mL of dioxane). The reaction was allowed to stir for 5 h at RT before quenching on to ice (80 g). The mixture was extracted with DCM (3×50 mL) and the combined organic layers were dried over Na$_2$SO$_4$ and concentrated under reduced pressure. The crude product was purified by chromatography (hexane) to afford 2,2,7,8-tetramethyl-5-(3-methyl-but-2-enyl)-chroman-6-ol as a light brown oil (229 mg). $^1$H-NMR (300 MHz, CDCl$_3$) δ (ppm): 5.16 (m, 1H), 4.70 (s, 1H), 3.34 (d, J=6.8 (2H), 2.18 (s, 3H), 2.14 (s, 3H), 1.86 (s, 3H), 1.81 (t, J=13.8, 2H), 1.77 (s, 3H), 1.32 (s, 6H); $^{13}$C-NMR δ (ppm): 145.7, 145.4, 134.1, 123.5, 122.2, 122.0, 121.8, 116.3, 72.5, 33.1, 26.7, 25.8, 20.8, 17.9, 12.1, 11.9; (ESI) m/z: 275 (M+H$^+$, 100%).

Example 4

2,2,7,8-Tetramethyl-5-(2-pyridin-3-yl-vinyl)-chroman-6-ol

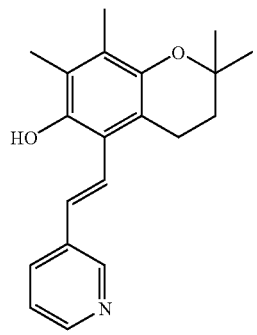

Step 1

A solution of Br$_2$ (0.540 mL, 10.5 mmol) in hexane (70 mL) was quickly added to the round bottom flask equipped with a CaCl$_2$ drying tube and containing a stirred solution of 2,2,5,7,8-pentamethyl-6-chromanol (2.20 g, 10.0 mmol) in hexane (340 mL). After stirring the reaction mixture for 2 h the solvents were evaporated yielding of 5-bromomethyl-2,2,7,8-tetramethyl-chroman-6-ol as a pale yellow solid (3.0 g), which was immediately used in the next step without further purification. $^1$H-NMR (300 MHz, CDCl$_3$) δ (ppm): 4.68 (s, 2H), 2.81 (t, J=7, 2H), 2.17 (s, 3H), 2.14 (s, 3H), 1.84 (t, J=7, 2H), 1.32 (s, 6H). MS (ESI-Pos) m/z 219.2 (M-Br$^+$).

Step 2

A solution of 5-bromomethyl-2,2,7,8-tetramethyl-chroman-6-ol (3.0 g, 10.0 mmol) and triphenylphosphine (2.62 g, 10.0 mmol) in toluene (100 mL) was stirred under reflux for 2.5 h producing white solid. Upon cooling the reaction mixture was filtered and the white solid washed with a small portion of toluene and dried under high vacuum to yield of the phosphonium salt derivative (5.36 g). $^1$H-NMR (300 MHz, CDCl$_3$) δ (ppm): 7.65-7.72 (m, 3H), 7.50-7.58 (m, 12H), 4.97 (d, J=13, 2H), 2.18 (t, J=7, 2H), 2.01 (d, J=3, 3H), 1.96 (s, 3H), 1.46 (t, J=7, 2H), 1.10 (s, 6H). MS (ESI-Pos) m/z 481.2 (M-Br$^+$)

Step 3:

A solution of phosphonium salt derivative from Step 2 (4.00 g, 7.12 mmol) in CH2Cl2 (250 mL) was treated with chloromethyl methyl ether (1.44 mL, 19.0 mmol) followed by diisopropyl ethyl amine (3.50 mL, 20.0 mmol). Upon stirring for 3 days, the reaction mixture was poured into water and shaken vigorously. Upon layer separation, the organic phase was removed and solvents evaporated producing the protected hydroxy derivative as a yellow foam/oil (4.34 g). $^1$H-NMR (300 MHz, CDCl$_3$) δ (ppm): 7.35-7.82 (m, 15H), 5.00 (d, J=14, 2H), 4.73 (s, 2H), 3.33 (s, 3H), 2.34 (br s, 2H), 2.05 (d, J=3, 3H), 1.89 (s, 3H), 1.47 (t, J=6, 2H), 1.08 (s, 6H).

Step 4:

A solution of the compound of Step 3 (908 mg, 1.50 mmol) in DMF (17 mL) was treated with NaH (66 mg, 1.65 mmol), stirred for 1 min and treated with 3-pyridinecarboxaldehyde (0.212 mL, 2.25 mmol). The reaction mixture was stirred for 6.5 h and quenched with H$_2$O. Solvents were evaporated and the residue was loaded onto silica gel. Column chromatography (SiO$_2$:hexane:EtOAc, 8:2 v/v) yielded 3-[2-(6-methoxymethoxy-2,2,7,8-tetramethyl-chroman-5-yl)-vinyl]-pyridine as a yellow oil (293 mg, 55%). $^1$H-NMR (300 MHz, CDCl$_3$) δ (ppm): 8.66-8.71 (m, 1H), 8.41-8.46 (m, 1H), 7.75-7.82 (m, 1H), 7.20-7.26 (m, 1H), 7.21 (d, J=16, 1H), 6.95 (d, J=16, 1H), 4.81 (s, 2H), 3.47 (s, 3H), 2.77 (t, J=7, 2H), 2.20 (s, 3H), 2.10 (s, 3H), 1.73 (t, J=7, 2H), 1.29 (s, 6H). MS (ESI-Pos) m/z 354.2 (M+H$^+$).

Step 7:

A solution of 3-[2-(6-methoxymethoxy-2,2,7,8-tetramethyl-chroman-5-yl)-vinyl]-pyridine (263 mg, 0.74 mmol) in MeOH (30 mL) was treated with conc. HCl (4.10 mL) and H$_2$O (0.5 mL). After stirring for 2.5 h the reaction mixture was poured into H$_2$O, followed by evaporation of MeOH, extraction with EtOAc and evaporation 2,2,7,8-Tetramethyl-5-(2-pyridin-3-yl-vinyl)-chroman-6-ol as a pale yellow oil (210 mg) Similarly by substituting 3-pyridinecarboxaldehyde with benzaldehyde in Step 4 and following the procedure described above, the following compounds were produced:

Similarly by substituting 3-pyridinecarboxaldehyde with benzaldehyde and following the procedure described herein 2,2,7,8-tetramethyl-5-styryl-chroman-6-ol was produced. $^1$H-NMR (300 MHz, CDCl$_3$) δ (ppm): 7.49-7.55 (m, 2H), 7.34-7.41 (m, 2H), 7.23-7.31 (m, 1H), 7.16 (d, J=16, 1H), 6.99 (d, J=16, 1H), 4.86 (s, 2H), 3.53 (s, 3H), 2.62 (t, J=7, 2H), 2.26 (s, 3H), 2.16 (s, 3H), 1.81 (t, J=7, 2H), 1.35 (s, 6H). MS (ESI-Pos) m/z 353.2 (M+H$^+$)

Thiazolecarboxaldehyde gave 2,2,7,8-tetramethyl-5-(2-thiazol-2-yl-vinyl)-chroman-6-ol MS (ESI-Pos) m/z 316.2 (M+H$^+$).

Similarly by substituting trans-cinnamaldehyde with thiazolecarboxaldehyde in Step 4 and following the procedure described above produced:

2,2,7,8-tetramethyl-5-(4-phenyl-butyl)-chroman-6-ol; $^1$H-NMR (300 MHz, CDCl$_3$) δ (ppm): 7.21-7.34 (m, 5H), 4.20 (s, 1H), 2.60-2.73 (m, 6H), 2.19 (s, 3H), 2.15 (s, 3H), 1.80 (t, J=6.8, 2H), 1.73-1.80 (m, 2H), 1.55-1.64 (m, 2H), 1.32 (s, 6H); MS (ESI-Pos) m/z 339.3 (M+H$^+$).

Example 5

5-(4,6-Dimethyl-pyrimidin-2-ylsulfanylmethyl)-2,7,8-trimethyl-2-(4,8,12-trimethyl-tridecyl)-chroman-6-ol

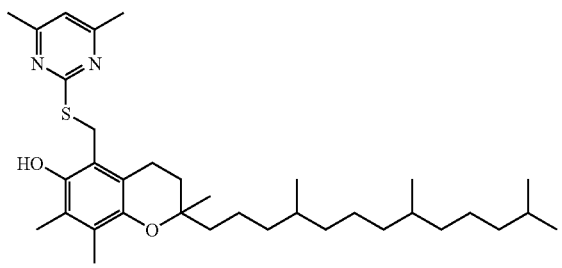

Step 1:

To a solution of α-tocopherol (5.0 g, 11.61 mmol) in 200 mL of dry hexane was added bromine (0.62 mL, 12.1 mmol) in 50 mL of dry hexane. The reaction mixture was allowed to stir at room temperature for 2 hours. Proton NMR indicated that the reaction was complete. After the solvent was removed in vacuo, the residue was used directly in the next step without further purification.

Step 2:

To a solution of bromo-α-tocopherol (crude product from above, 2.32 mmol) in 10 mL of CH$_2$Cl$_2$ was added sodium bicarbonate (0.2 g) and 4,6-dimethyl-pyrimidine-2-thiol (3.63 mmol). The reaction was allowed to stir at room temperature overnight. After more CH$_2$Cl$_2$ was added, the reaction mixture was washed with water, dried over anhydrous MgSO$_4$, and concentrated in vacuo. The residue was purified by flash chromatography eluted with 2% MeOH in CH$_2$Cl$_2$ to give 5-(4,6-Dimethyl-pyrimidin-2-ylsulfanylmethyl)-2,7,8-trimethyl-2-(4,8,12-trimethyl-tridecyl)-chroman-6-ol, $^1$H-NMR (300 MHz, CDCl$_3$) δ (ppm): 9.96 (s, 1H), 6.73 (s, 1H), 4.31 (m, 2H), 2.75 (t, 2H), 2.48 (s, 6H), 2.22 (s, 3H), 2.11 (s, 3H)), 1.90 (m, 2H), 1.70-0.84 (m, 36H). $^{13}$C-NMR (75 MHz, CDCl$_3$) δ (ppm): 171.65, 167.42, 145.73, 145.57, 125.69, 124.66, 120.48, 116.82, 116.03, 74.57, 40.0, 39.47, 37.56, 37.39, 32.87, 32.77, 31.0, 28.06, 27.5, 24.92, 24.55, 23.86, 23.43, 22.87, 22.77, 21.12, 19.88, 19.78, 12.70, 12.14; MS: m/z=569.3 (M+H$^+$).

Similarly by substituting 4,6-dimethyl-pyrimidine-2-thiol for other thiols the following compounds were produced:

2,7,8-trimethyl-5-(5-methyl-1H-benzoimidazol-2-ylsulfanylmethyl)-2-(4,8,12-trimethyl-tridecyl)-chroman-6-ol, $^1$H-NMR (300 MHz, CDCl$_3$) δ (ppm): 7.27 (b, 2H), 6.97 (d, 1H), 4.50 (m, 2H), 2.70 (t, 2H), 2.42 (s, 3H), 2.27 (s, 3H), 2.11 (s, 3H), 1.82, (m, 2H), 1.70-0.85 (m, 36H). $^{13}$C-NMR (75 MHz, CDCl$_3$) δ (ppm): 151.72, 145.99, 145.78, 132.12, 126.34, 126.14, 123.71, 121.15, 116.91, 74.73, 40.0, 39.49, 37.58, 37.41, 32.91, 32.85, 31.0, 28.5, 28.10, 24.94, 24.59, 23.73, 22.88, 22.78, 21.60, 21.14, 19.89, 19.78, 13.17, 12.29. MS: m/z=593.4 (M+H$^+$).

4-[2-(4,8-Dimethyl-tridecyl)-6-hydroxy-2,7,8-trimethyl-chroman-5-ylmethylsulfanyl]-benzoic acid, $^1$H-NMR (300 MHz, CDCl$_3$) δ (ppm): 8.03 (d, 2H), 7.42 (d, 2H), 4.31 (s, 2H), 2.77 (t, 2H), 2.19 (s, 3H), 2.14 (s, 3H), 1.78 (m, 2H), 1.70-0.84 (m, 36H). $^{13}$C-NMR (75 MHz, CDCl$_3$) δ (ppm): 172.0, 146.11, 145.73, 145.33, 130.55, 126.99, 126.12, 125.82, 122.68, 117.63, 116.60, 74.92, 39.86, 39.42, 37.51, 37.34, 32.86, 32.73, 31.50, 29.0, 28.03, 24.87, 24.51, 23.81, 22.80, 22.70, 21.05, 19.82, 19.72, 12.29, 12.19. MS: m/z=583.3 (M+H$^+$).

1-{3-[6-Hydroxy-2,7,8-trimethyl-2-(4,8,12-trimethyl-tridecyl)-chroman-5-ylmethylsulfanyl]-2-methyl-propionyl}-pyrrolidine-2-carboxylic acid, $^1$H-NMR (300 MHz, CDCl$_3$) δ (ppm): 2.15 (s, 3H), 2.09 (s, 3H). $^{13}$CNMR (75 MHz, CDCl$_3$) δ (ppm): 176.1, 174.7, 145.9, 145.6, 125.1, 123.3, 118.8, 116.9, 74.6, 59.4, 47.4, 39.4, 37.4, 37.3, 32.8, 32.7, 28.0, 24.8, 24.5, 23.7, 22.8, 21.0, 19.8, 19.7, 17.4, 12.4, 12.0. MS (API-ES) m/z 646 (M+H$^+$, 27%), 668 (M+Na$^+$, 100%).

Similarly by substituting α-tocopherol for 2,2,5,7,8-Pentamethyl-chroman-6-ol, and using different thiols the following compound was prepared:

1-[3-(6-Hydroxy-2,2,7,8-tetramethyl-chroman-5-ylmethylsulfanyl)-2-methyl-propionyl]-pyrrolidine-2-carboxylic acid $^1$H-NMR (300 MHz, CDCl$_3$) δ (ppm): 4.60 (m, 1H), 3.53-3.93 (m, 2H), 3.52 (m, 2H), 2.56-2.85 (m, 5H), 2.20 (s, 3H), 2.17 (s, 3H), 2.20-1.76 (m, 6H), 1.28 (s, 6H), 1.17 (d, 2H); $^{13}$C-NMR (75 MHz, CDCl$_3$) δ (ppm): 176.08, 174.74, 145.92, 145.76, 125.11, 123.47, 118.89, 116.68, 72.61, 59.94, 47.39, 39.82, 34.62, 32.93, 29.05, 28.37, 26.72, 24.74, 20.39, 17.67, 12.40, 12.07. MS: m/z=436.2 (M+H$^+$), 458.2 (M+Na$^+$).

Example 6

5-[3-(6-Hydroxy-2,7,8-trimethyl-chroman-2-yl)-propylidene]-thiazolidine-2,4-dione

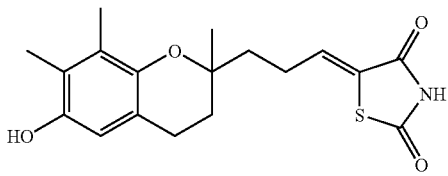

Step 1:

A mixture of 3-(6-hydroxy-2,7,8-trimethyl-chroman-2-yl)-propionic acid (500 mg), 3,4-dihydro-2-H-pyran (2 mL) and pyridinium p-toluenesulfonate (PPTS) (50 mg) in dichloromethane (20 mL) was stirred at RT for overnight. The mixture was washed with water, dried over $MgSO_4$, and concentrated to give an oily residue. The oil was dissolved in THF, then $LiAlH_4$ (85 mg) was added and the mixture was stirred at RT for 2 h. The excess $LiAlH_4$ was destroyed by adding ethyl acetate, and the mixture was poured into water and extracted with EtOAc. The organic layer was washed with water, dried over $MgSO_4$, and concentrated. The residue was purified by silica gel column chromatography eluting with 30% EtOAc in hexane to give 732 mg of 3-[2,7,8-trimethyl-6-(tetrahydro-pyran-2-yloxy)-chroman-2-yl]-propan-1-ol as an oily product. $^1$H-NMR (300 MHz, $CDCl_3$) δ (ppm): 6.67 (s, 1H), 5.32 (t, J=3.2 MHz, 1H), 4.0-3.9 (m, 1H), 3.70-3.55 (m, 3H), 2.75-2.70 (m, 2H), 2.15, 2.09 (2s, 6H), 2.10-1.60 (m, 12H), 1.25 (s, 3H). $^{13}$C-NMR (75 MHz, $CDCl_3$) δ (ppm): 148.08, 146.23, 125.51, 125.25, 117.66, 112.99, 112.96, 97.36, 75.17, 63.25, 62.09, 60.41, 36.26, 36.03, 31.51, 31.47, 30.78, 26.97, 25.41, 24.01, 23.81, 22, 48, 21.05, 19.11, 14.19, 12.18, 11.94.

Step 2:

A mixture of 3-[2,7,8-trimethyl-6-(tetrahydro-pyran-2-yloxy)-chroman-2-yl]-propan-1-ol (200 mg), pyridinium chlorochromate (PCC) (350 mg), and 4 A° molecular sieves (100 mg) in dichloromethane (15 mL) was stirred at RT for overnight. The mixture was passed through a silica gel column chromatography eluting with 30% EtOAc in hexane to give 40 mg of 3-[2,7,8-trimethyl-6-(tetrahydro-pyran-2-yloxy)-chroman-2-yl]-propionaldehyde as an oily product. $^1$H-NMR (300 MHz, $CDCl_3$) δ (ppm): 9.79 (s, 1H, CHO), 6.67 (s, 1H), 5.23 (d, J=2.2 MHz, 1H), 3.90 (m, 1H), 3.58 (m, 1H), 2.75-2.60 (m, 4H), 2.15, 2.08 (2s, 6H), 2.00-1.58 (m, 10H), 1.23 (s, 3H). $^{13}$C-NMR ($CDCl_3$, 75 MHz) δ (ppm): 202.64, 148.26, 145.87, 125.57, 125.41, 117.39, 112.93, 112.87, 97.34, 97.22, 74.33, 62.11, 62.05, 38.58, 32.34, 32.09, 31.60, 31.53, 30.76, 25.41, 23.85, 23.64, 22.36, 19.11, 19.08, 12.11, 11.96. MS (m/z): 333 (MH$^+$), 355 (M+Na$^+$).

Step 3:

A mixture of 3-[2,7,8-trimethyl-6-(tetrahydro-pyran-2-yloxy)-chroman-2-yl]-propionaldehyde (145 mg) from Step 2,2,4-thiazolidinedione (90 mg), piperidine (0.02 mL), and benzoic acid (16 mg) in toluene (15 mL) was refluxed at 140° C. for 3 h. The mixture was then cooled down and concentrated. The residue was purified directly by silica gel column chromatography eluting with 50% EtOAc in hexane to give 155 mg 5-{3-[2,7,8-trimethyl-6-(tetrahydro-pyran-2-yloxy)-chroman-2-yl]-propylidene}-thiazolidine-2,4-dione as a yellow oil. $^1$H-NMR (300 MHz, $CDCl_3$) δ (ppm): 8.50 (br, 1H), 7.07 (m, 1H), 6.67 (s, 1H), 5.24 (s, 1H), 3.95 (m, 1H), 3.58 (m, 1H), 2.72 (m, 2H), 2.38 (m, 2H), 2.16, 2.10 (2s, 6H), 2.00-1.55 (m, 10H), 1.25 (s, 3H). MS (m/z): 432 (M+H$^+$), 454 (M+Na$^+$).

Step 4:

To a solution of 5-{3-[2,7,8-trimethyl-6-(tetrahydro-pyran-2-yloxy)-chroman-2-yl]-propylidene}-thiazolidine-2,4-dione from Step 3 (155 mg) in MeOH (10 mL) were added 10 drops of conc. HCl, and the mixture was stirred at RT for 3 h, then poured into water and extracted with EtOAc. The crude product was purified by silica gel column chromatography eluting with 30-40% EtOAc in hexane to give 5-[3-(6-hydroxy-2,7,8-trimethyl-chroman-2-yl)-propylidene]-thiazolidine-2,4-dione. $^1$H-NMR (300 MHz, $CDCl_3$) δ (ppm): 7.08 (t, J=7.6 MHz, 1H), 6.38 (s, 1H), 2.70 (m, 2H), 2.37 (m, 2H), 2.14, 2.11 (2s, 6H), 2.00-0.180 (m, 4H), 1.25 (s, 3H) ppm. $^{13}$C-NMR (75 MHz, $CDCl_3$) δ (ppm): 171.45, 167.17, 165.43, 146.63, 145.06, 139.75, 126.04, 125.86, 122.03, 117.81, 112.20, 74.41, 60.53, 37.52, 31.51, 26.30, 23.74, 22.06, 21.09, 14.18, 12.00, 11.90 ppm. MS (m/z): 348 (M+H$^+$), 370 (M+Na$^+$).

Alternatively, the protection of the hydroxy group in Step 1, was also carried out with chloromethylmethyl ether in the presence of sodium hydride in DMF to give the MOM protected product. The removal of the protective group MOM was carried out under the same conditions as in Step 4, but required additional time (overnight).

Similarly, starting from 6-hydroxy-2,7,8-trimethyl-2-(4,8,12-trimethyl-tridecyl)-chroman-5-carbaldehyde and following the procedure described above 5-[6-Hydroxy-2,7,8-trimethyl-2-(4,8,12-trimethyl-tridecyl)-chroman-5-ylmethylene]-thiazolidine-2,4-dione was produced. $^1$H-NMR (300 MHz, $CDCl_3$) δ (ppm): 7.95 (s, 1H), 2.93 (t, J=6.8 Hz, 2H), 2.43 (s, 3H), 2.27 (s, 3H), 1.95-1.90 (m, 2H), 1.85-1.00 (m, 26H), 0.90-0.82 (m, 12H). $^{13}$C-NMR (300 MHz, $CDCl_6$) δ (ppm): 176.6, 174.5, 149.5, 143.9, 132.7, 127.7, 126.6, 124.4, 116.8, 112.2, 76.5, 39.6, 39.4, 37.43, 37.37, 32.8, 32.6, 28.0, 24.8, 24.4, 23.7, 22.7, 20.9, 19.8, 19.7, 12.9, 11.8.

Example 7

1-(6-Hydroxy-2,7,8-trimethyl-chroman-2-yl)-3-bis-(5-methyl-2-phenyl-2,4-dihydro-pyrazol-3-one-4-yl)-propane

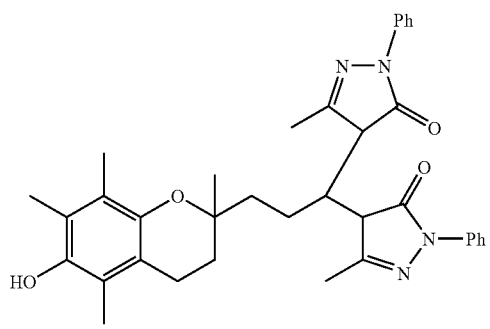

A mixture of 3-(6-methoxymethoxy-2,7,8-trimethyl-chroman-2-yl)-propionaldehyde (200 mg) prepared as described herein, 5-methyl-2-phenyl-2,4-dihydro-pyrazol-3-one (150 mg), piperidine (0.02 mL) and benzoic acid (20 mg) in toluene (20 mL) was refluxed at 140° C. for 2 h. The mixture was concentrated to dryness and the residue was purified by silica gel column chromatography eluting with 3-5% MeOH in DCM to give 280 mg of 4-[3-(6-methoxymethoxy-2,7,8-trimethyl-chroman-2-yl)-1,1-di-(3-methyl-5-oxo-4,5-dihydro-1H-pyrazol-4-yl)-propane as a brown solid. $^1$H-NMR (300 MHz, CDCl$_3$) δ (ppm): 7.55 (d, J=6.6, 4H), 7.24 (t, J=6.6, 4H), 7.06 (t, J=7.2, 2H), 6.58 (s, 1H), 5.00 (s, 2H), 3.47 (s, 3H), 3.15 (t, 1H), 2.63 (m, 2H), 2.09, 2.06, 1.90, 1.88 (4s, 12H), 2.20-1.40 (m, 8H), 1.19, 0.88 (2s, 6H). $^{13}$C-NMR (75 MHz, CDCl$_3$) δ (ppm): 148.12, 146.65, 128.88, 126.08, 125.72, 125.32, 121.42, 121.26, 117.87, 113.02, 95.76, 75.49, 55.99, 31.59, 30.01, 24.00, 22.66, 22.42, 14.14, 12.15, 12.04, 11.56, 11.50. MS (m/z): 623 (MH$^+$, 100%).

A mixture of 4-[3-(6-methoxymethoxy-2,7,8-trimethyl-chroman-2-yl)-1,1-di-(3-methyl-5-oxo-4,5-dihydro-1H-pyrazol-4-yl)-propane (200 mg) in MeOH with a few drops of conc. HCl was stirred at RT for overnight. Then it was poured into water and extracted with EtOAc. The organic layer was washed with water and brine, dried over MgSO4, and concentrated. The residue was purified by silica gel column chromatography eluting with 3.5-7.5% MeOH in DCM to give 1-(6-hydroxy-2,7,8-trimethyl-chroman-2-yl)-3-bis-(5-methyl-2-phenyl-2,4-dihydro-pyrazol-3-one-4-yl)-propane as a brown solid (100 mg). $^1$H-NMR (300 MHz, CDCl$_3$-CD$_3$OD) δ (ppm): 7.62 (d, J=7.7, 4H), 7.35 (m, 4H), 7.20 (m, 2H), 6.33 (m, 1H), 3.36 (t, 2H), 2.60 (m, 2H), 2.21, 2.19, 2.08, 2.06 (4s, 12H), 2.40-1.80 (m, 3H), 1.60-1.40 (2m, 4H), 1.35 (s, 3H). $^{13}$C-NMR (75 MHz, CDCl$_3$-CD$_3$OD) δ (ppm): 146.74, 145.00, 128.83, 126.04, 125.54, 122.03, 121.47, 121.36, 118.10, 111.94, 75.34, 38.10, 31.26, 30.04, 25.68, 24.05, 22.14, 11.89, 11.79, 11.49.

Example 8

2,2,7,8-Tetramethyl-5-(3-nitro-phenyl)-chroman-6-ol

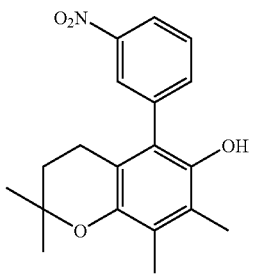

A mixture of 5-bromo-2,2,7,8-tetramethyl-chroman-6-ol (400 mg, 1.40 mmol), 3-nitrophenyl boronic acid (300 mg, and Pd(PPh3)4 (100 mg, 5% mol) in glycol dimethyl ether (DME, 20 mL) and 2M Na$_2$CO$_3$ solution (5 mL) was stirred at 120° C. for 3-5 h. After pouring it into water, the mixture was extracted with EtOAc. The EtOAc layer was washed with water, dried and concentrated. The residue was purified by silica gel column chromatography eluting with 10% EtOAc in hexane to give a yellow solid (140 mg). $^1$H NMR (300 MHz, CDCl$_3$): 8.25-8.16 (μ, 2H), 6.76 (μ, 2H), 4.13 (σ, 1H, OH), 2.27 (μ, 2H), 2.21, 2.19 (2σ, 6H), 1.68 (μ, 2H), 1.32 (σ, 6H) ppm. $^{13}$C NMR (75 MHz, CDCl$_3$) δ: 167.36, 148.79, 145.85, 143.34, 138.27, 136.95, 130.10, 126.51, 125.56, 122.76, 122.29, 115.84, 73.10, 32.83, 27.07, 26.71, 12.95, 12.24, 12.14 ppm. MS: m/z: 328 (MH$^+$).

Example 9

8-Chloro-2-(2,5-dimethyl-thiophen-3-yl)-2,5,7-trimethyl-chroman-6-ol

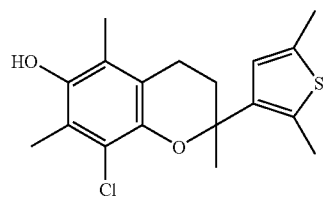

Step 1:
A mixture of 2,6-dimethyl-[1,4]benzoquinone (5 g) and sodium hydrosulfite (10 g) in EtOAc (50 mL) and water (20 mL) was stirred for 30 min. After separation with EtOAc, the organic phase was dried and evaporated to dryness to give a off-white solid 5 g of 2,6-dimethyl-benzene-1,4-diol. The solid was dissolved in dry ether, cooled in an ice-water bath, followed by dropwise addition of sulfuryl chloride (5 g). After stirring the solution at RT for 3 h, workup and purification on silica gel column chromatography (30% EtOAc in hexane) gave 2.2 g 2-chloro-3,5-dimethyl-benzene-1,4-diol.
Step 2:
To a solution of 2-chloro-3,5-dimethyl-benzene-1,4-diol (520 mg) and BF3 etherate (1.28 g) in dioxane (10 mL) at 120° C. was added slowly a solution of the vinyl alcohol 2-(2,5-dimethyl-thiophen-3-yl)-but-3-en-2-ol (600 mg) in 2 mL of dioxane in 30 min. After completion, the solution was stirred at 120° C. for 3 h. Workup and purification by silica gel column chromatography eluting with 10% EtOAc in hexane gave 50 mg off-white solid 4-Chloro-6-(2,5-dimethyl-thiophen-3-yl)-1,3,6-trimethyl-5,6,7,8-tetrahydro-naphthalen-2-ol. $^1$H NMR (300 MHz, CDCl$_3$) δ: 6.52 (s, 1H), 4.29 (s, 1H, OH), 2.63-2.33 (3s+m, 12H), 2.06-2.01 (s+m, 4H), 1.62 (s, 3H) ppm. $^{13}$C NMR (75 MHz, CDCl$_3$ δ: 145.40, 143.98, 139.90, 134.97, 132.28, 125.68, 121.24, 120.34, 119.97, 119.57, 78.05, 32.85, 28.52, 21.74, 15.49, 14.96, 13.49, 11.77 ppm. MS m/z: 337 (M+H$^+$).

Example 10

2-(2,2-Dichloro-vinyl)-2,5,7,8-tetramethyl-chroman-6-ol

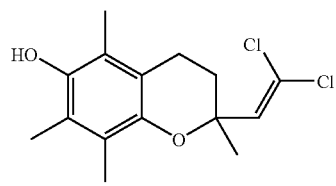

A mixture of triphenylphosphine (524 mg, 2.0 mmol), carbon tetrachloride (193 ul, 2.0 mmol), Zinc dust (130 mg, 2.0 mmol) and 6-methoxymethoxy-2,5,7,8-tetramethyl-chroman-2-carbaldehyde (0.25 gram, 0.95 mmol) in 4 ml of DCM was stirred overnight at room temperature. The mixture was rinsed with hexane times and the combined solutions were dried over MgSO4. The solution was concentrated and the residue was purified via flash column chromatography on silica gel (10% ethyl acetate in hexane) to afford 320 mg of 2-(2,2-dichloro-vinyl)-6-methoxymethoxy-2,5,7,8-tetramethyl-chroman.

A solution 160 mg of 2-(2,2-dichloro-vinyl)-6-methoxymethoxy-2,5,7,8-tetramethyl-chroman in 5 ml of methanol and 0.1 ml of conc. HCl was stirred overnight. The methanol was removed and the residue was mixed with ethyl acetate and water. Regular work-up and flash column chromatography on silica gel (15% ethyl acetate in hexane) afforded 70 mg of 2-(2,2-Dichloro-vinyl)-2,5,7,8-tetramethyl-chroman-6-ol. NMR (1H, CDCl$_3$): 6.01 (1H, s), 4.26 (1H, s), 2.63 (2H, m), 2.48 (1H, m), 2.19 (3H, s), 2.16 (3H, s), 2.13 (3H, s), 1.78 (1H, m), 1.62 (3H, s). LC-MS: 301 (M+H, 100%), 323 (M+Na, 78%)

Example 11

MPP+ Cell Death Assay

Media Composition

RF media: DMEM-No glucose, glucose (29.1 mM), L-glutamine (1.4 mM), 10% heat-inactivated FBS, and 1× penicillin/streptomycin (P/S)

Wash media: DMEM-No glucose and 1×P/S

Low serum media: DMEM-No glucose, glucose (29.1 mM), L-glutamine (1.4 mM), 0.5% FBS, and 1×P/S Assay Media: DMEM-No glucose, L-glutamine (1.4 mM), 0.5% FBS, and 1×P/S Experimental Procedure The substantia nigra-derived dopaminergic progenitor cell line was seeded in poly-D-lysine-coated 24-well plates at a density of 4500 cells per well in RF media. The cells were left to attach for 16 hours in a 33° C. incubator (5% $CO_2$) after which time they were washed once with 500 pL wash media and then differentiated into a neuronal phenotype by incubating in low serum media for 24 hours in a 39° C. incubator (5% $CO_2$).

After 24 hours the low serum medium was aspirated from the cells and the monolayer was washed once with 500 μL wash media. Test articles were diluted to 2-fold the desired testing concentration in assay media and 250 μL was added to the cells. From a 10 mM stock, a working solution of 140 μM 1-methyl-4-phenylpyridinium (MPP$^+$) (Sigma, St. Louis, Mo.) was made in assay media and 250 μL of this working solution was also added to the cells. The final volume in each well was 500 μL and the final concentration of MPP$^+$ was 70 μM. As a negative control, cells were incubated with 500 μL assay media with no additions.

Cells were incubated in a 39° C. incubator (5% $CO_2$) for 24 hours. After this time, the number of live neurons remaining in each well was determined using a fluorescent vital cell stain, Cell Tracker Green (Molecular Probes, Eugene, Oreg.). Assay media was aspirated from the cells and 400 pL of 2.5 μM Cell Tracker Green was added to each well. Cells were placed in a 37° C. incubator for 5 minutes after which time the cell stain was aspirated off and 500 μL of HBSS (Invitrogen Life Technologies, Carlsbad, Calif.) was added to each well. The number of live cells in each well was then quantitated using an automated fluorescent microscope/imaging system (Universal Imaging, Downingtown Pa.).

Results:

Certain compounds of the present invention such as 2-[6-Hydroxy-2,7,8-trimethyl-2-(4,8,12-trimethyl-tridecyl)-chroman-5-ylmethylsulfanyl]-ethanesulfonic acid;

5-(4,6-Dimethyl-pyrimidin-2-ylsulfanylmethyl)-2,2,7,8-tetramethyl-chroman-6-ol;
5-Hexylsulfanylmethyl-2,2,7,8-tetramethyl-chroman-6-ol;
5-Allylsulfanylmethyl-2,2,7,8-tetramethyl-chroman-6-ol;
5-Cyclopentylsulfanylmethyl-2,2,7,8-tetramethyl-chroman-6-ol when tested as described above provided protection in at least 30%, preferably in at least 50% of the cells tested at concentrations ranging from about 1 to 25 μM.

Example 12

FRDA Fibroblast Assay for Protection from Oxidative Stress

A. Cell Culture and Reagents

Primary fibroblasts were derived from donors with a molecular diagnosis of FRDA and control donors with no mitochondria) disease. Lines F2, C2 and C3 were obtained from Coriell Cell Repositories (Camden, N.J., USA; catalog nos GM04078, GM08402 and GM08399, respectively). All cell types were diagnosed at the molecular level for intronic GAA triplet repeat length in the frataxin gene using a PCR-based method, according to methods known in the art. FRDA-fibroblasts types had ~400-450 repeats (F2 line) or more (F1 and F3), whereas control cell lines displayed repeats of normal length. The cells were seeded in 96-well plates at a density of 4000 cells per 100 pl in growth medium consisting of 25% (v/v) M199 EBS and 64% (v/v) MEM EBS without phenol red (Bioconcept, Allschwil, Switzerland) supplemented with 10% (v/v) fetal calf serum (PAA Laboratories, Linz, Austria), 100 U/ml penicillin, 100 μg/ml streptomycin (PAA Laboratories, Linz, Austria), 10 μg/ml insulin (Sigma, Buchs, Switzerland), 10 ng/ml EGF (Sigma, Buchs, Switzerland), 10 ng/ml bFGF (PreproTech, Rocky Hill, N.J., USA) and 2 mM glutamine (Sigma, Buchs, Switzerland). The cells were incubated in the presence of the various test compounds for 24 h before addition of 1 mM BSO (L-buthionine (S,R)-sulfoximine).

B. Cell Viability Measurements

Cell viability was measured after the first signs of toxicity appeared in the BSO-treated controls (typically after 16-48 h). The cells were stained for 60 min at room temperature in PBS with 1.2 μm calceinAM and 4 pm ethidium homodimer (Live/Dead assay, Molecular Probes, Eugene, Oreg., USA). Fluorescence intensity was measured with a Gemini Spectramax XS spectrofluorimeter (Molecular Devices, Sunnyvale, Calif., USA) using excitation and emission wavelengths of 485 and 525 nm, respectively.

C. Data and Statistics

In experiments carried out in support of the present invention, certain compounds such as 1-{3-[6-Hydroxy-2,7,8-trimethyl-2-(4,8,12-trimethyl-tridecyl)-chroman-5-ylmethylsulfanyl]-2-methyl-propionyl}-pyrrolidine-2-carboxylic acid;
5-[3-(6-Hydroxy-2,7,8-trimethyl-chroman-2-yl)-propylidene]-thiazolidine-2,4-dione;
1-(6-Hydroxy-2,7,8-trimethyl-chroman-2-yl)-3-bis-(5-methyl-2-phenyl-2,4-dihydro-pyrazol-3-one-4-yl)-propane;
5-Hexylsulfanylmethyl-2,2,7,8-tetramethyl-chroman-6-ol;
5-Allylsulfanylmethyl-2,2,7,8-tetramethyl-chroman-6-ol;
5-Cyclopentylsulfanylmethyl-2,2,7,8-tetramethyl-chroman-6-ol;

significantly reduced cell death in FRDA fibroblasts compared to untreated FRDA fibroblasts with an $EC_{50}$ of between about 0.01 μM and 6 μM.

Example 13

Rat Middle Cerebral Artery Occlusion (MCAO) Model of Cerebral Ischemia

A. Animal Preparation

Male Wistar rats (Harlan, Ind.) weighing 300-350 g are commonly used in these experiments. Animals are allowed free access to water and commercial rodent diet under standard laboratory conditions. Room temperature is maintained at 20-23° C. and room illumination is on a 12/12-hour light/dark cycle. Animals are acclimatized to the laboratory environment 5 to 7 days prior to the study, and fasted (with free access to water) overnight before surgery.

B. Middle Cerebral Artery Occlusion (MCAO)

Anesthesia is maintained by inhalation of 3.0% isoflurane (Aerrane, Front Dodge, Iowa) in 0.8% oxygen. The animal's neck is shaved and sterilized before operation. Body temperatures are controlled and maintained at 37.5° C.+/−1 degree via external heating and cooling devices. To lower the body temperature, animals are placed in a cooling chamber, which uses ice to cool circulating air. Throughout the study the body temperature is recorded using a temperature transponder (BMDS Inc., Seaford, DL) implanted subcutaneously at the time of MCAO between the rat shoulder blades that allows the user to read the body temperature via a pocket scanner (BMDS Inc., Seaford, DL). The body temperature is taken by inserting the temperature probe into the animal's rectum. Body temperature is recorded every hour for 6 hours post-occlusion; however, body temperatures are taken more frequently so that they could be maintained at the normothermic temperature.

Animals are subjected to two hours MCAO using a modified intraluminal filament technique, as follows: A midline incision on the ventral part of the neck is made to expose external and internal carotid arteries. The right external and common carotid arteries are ligated by a suture (silk 5/0, Carlisle Laboratories, Farmers Branch, Tex.) and the right internal artery is temporarily ligated using a microvascular clip (Fine Science Tool Inc., Foster City, Calif.). A small incision is made in the common carotid artery. A nylon filament, its tip rounded by heating, is prepared from a fishing line (Stren Fishing Lines, Wilmington, Del.) and is inserted from the right common carotid artery. The filament is advanced into the internal carotid artery 18-20 mm from the point of bifurcation of internal and external arteries and a suture is tightly ligated around the filament. Two hours post occlusion, animals are re-anesthetized to allow reperfusion for the remaining of the experiment by removal of the filament.

C. Drug Administration

Test compounds may be administered by any of a number of routes, such as those described below. Compounds can be administered before, during or after occlusion, as appropriate to the protocol.

a) Intracerebroventricular (ICV) Infusion

The anesthetized animal is placed on a stereotaxic apparatus (Harvard Apparatus, S. Natick, Mass.). Anesthesia is maintained by inhalation of 3.0% isoflurane (Aerrane, Front Dodge, Iowa) in 0.8% oxygen throughout the entire procedure. The scalp is shaved and sterilized prior to surgery. A midline sagittal incision about 3 cm long is made slightly behind the eyes to expose the skull. The skull is scraped with a rounded end spatula to remove periosteal connective tissue. A bur hole is placed 1.5 mm lateral, 1 mm posterior to the left of the bregma to mark the left lateral ventricle. A brain infusion cannula (ALZET Co., Palo Alto, Calif.) is inserted 4 mm deep into the hole. The desired depth is adjusted by attaching spacers to the cannula. The cannula attached to a 4-cm silastic catheter (Helix Medical Inc., Carpinteria, Calif.) fixed in place with dental cement (Ketac-cement, Norristown, Pa.). The catheter is either attached to a primed osmotic pump placed subcutaneously between the shoulder blades for permanent infusion or to a syringe for a short infusion.

b) Intravenous (IV) Osmotic Pump Implantation into the Jugular Vein

Anesthesia is maintained by inhalation of 3.0% isoflurane (Aerrane, Front Dodge, Iowa) in 0.8% oxygen throughout the entire procedure. The animal's neck will be shaved and sterilized before operation. A midline incision is made on the ventral part of the neck to exposes the jugular vein. The vein is isolated and ligated with a suture (silk 5/0, Carlisle Laboratories, Farmers Branch, Tex.) rostra) to the point of the incision and a microvascular clip (Fine Science Tool Inc., Foster City, Calif.) close to the heart. A small incision is made between two ligations. A 2-cm silastic catheter (Helix Medical Inc.) attached to a PE-60 tube (Becton. Dickinson and Co. Sparks, Md.) connected to an ALZET (ALZET CO. Palo Alto, Calif.) pump is introduced and advanced 2 mm into the jugular vein toward the heart. The microvascular clip is removed and the catheter is secured in place with a suture (silk 5/0, Carlisle Laboratories, Farmers Branch, Tex.). The pump is placed into a pocket made subcutaneously between the shoulder, blades, allowing the catheter to reach over neck to the jugular vein with sufficient slack to permit free movement of neck and head.

c) IV Infusion Via Femoral Vein

Anesthesia is maintained by inhalation of 3.0% isoflurane (Aerrane, Front Dodge, Iowa) in 0.8% oxygen throughout the entire procedure. The exterior site of the right femoral vein is shaved and sterilized prior to surgery. A 3-cm incision is made in the right groin region and the femoral vein is isolated. A small incision is made on the femoral vein temporarily ligated with a microvascular clip to introduce and advance a polyethylene (PE-50) catheter (Becton Dickinson and Co. Sparks, Md.). The catheter is secured in place with suture (silk 5/0, Carlisle Laboratories, Farmers Branch, Tex.). The other end of the catheter is attached to a syringe filled with the heparinized saline for the bolus injection. Using a hemostat, a pocket is made subcutaneously on the back of the animal so the PE catheter can be brought up to the exteriorization point at the nape of the neck for either a bolus injection or a continuous injection by an osmotic pump.

d) Intraperitoneal (IP) Injection

An awake rat is held in a standard hand hold position, a 23¾ G needle is injected into the lower right quarter of the abdomen pass the peritoneum, slightly off the midline. To avoid organ injection, the plunger of the syringe is slightly pulled back. If no fluid is withdrawn, the content of the syringe is delivered into the abdominal cavity.

e) Gavage Feeding

A standard rat gavage tube (Popper & Sons Inc., NY) is attached to a 3-cc hypodermic syringe. The animal is held by the shoulder in a vertical position. The feeding tube is placed into the mouth then advanced until it reaches the stomach (the approximate insertion length of the tube was measured prior to the feeding). The content of the syringe is slowly delivered, and then the tube is withdrawn.

D. Behavioral Assessment

One hour after MCAO, the animal is gently held by its tail and observed for forelimb flexion. Then the animal is placed on the floor to be observed for walking pattern; only the animals that score 3 on Bederson grading system (Table 1) are included in the study.

TABLE 1

Bederson Grading System for Neurological Evaluation

| Neurological deficit | Grading | Behavioral observation |
|---|---|---|
| Normal | grade 0: | No observable deficit |
| Moderate | grade 1: | forelimb flexion |
| Severe | grade 2: | forelimb flexion, decreased resistance to lateral push |
| Extreme | grade 3: | forelimb flexion, decreased resistance to lateral push, circle to paretic side |

E. Evaluation of Ischemic Damage

Twenty-four hours post-MCAO, or longer, in some experiments, animals are sacrificed by CO2 asphyxiation (dry ice). The brain is quickly removed from the skull, using standard procedures, rinsed in chilled saline solution, and placed on a rat brain tissue slicer (ASI instrument, MI). Seven 2-mm thick corona) slices are cut from each brain using razor blades. The slices are immersed in 0.9% saline containing 1.0% 2,3,5-triphenyltetrazolume chloride (TTC) (Sigma Chemical Co., St. Louis, Mo.) and incubated in a 37° C. water bath for 30 minutes.

After staining, each 2-mm slice is photographed with a TMC-7 camera (JH Technologies, Ca) which is directly connected to a desktop PC to capture and saved the image of each brain slice. This image is used for the measurements of the regions of interest using a computer-based image processing system (Metamorph).

To measure each area, the region of interest is selected using a freehand selection tool, the area is automatically computed by selecting the measure command. The measurements for primary regions of interest are right hemisphere, left hemisphere, total infarct, subcortical infarct, total penumbra and subcortical penumbra. After all regions of interest are measured for all seven slices of the brain, they are sorted by slice number and the corresponding regions of interest using a custom made Excel™ macro. This macro calculates the cortical penumbra, cortical infarct and total ischemic damage for each slice; the corresponding areas of each rat brain are added together to produce a single measurement for each area. Since the ipsilateral hemisphere is swollen following MCAO, edema volume is calculated and reported as the volumetric differences between the right and left hemispheres of each brain slice. Using the % of hemispheric swelling all the volumes are corrected for the edema.

The volume of the damage is determined using the calculations below for each rat's brain.

F. Statistical Analysis

Sample size is chosen to achieve a 90% probability of significant results. The measurements, which represent the same region of interest in seven slices of each rat's brain are added together to yield a single measurement for total infarct, subcortical infarct, cortical infarct, total penumbra, subcortical penumbra, cortical penumbra, total ischemic damage and edema in each animal. Group data is presented as means+/−SEM. Differences at the level of $p<0.05$ are considered statistically significant. Between groups comparisons of each region of interest are carried out by unpaired student t test (between two groups) or one way ANOVA followed by post hoc Bonferroni's multiple comparisons or by the nonparametric Dunnett's test (between control and the drug treated groups).

Test compounds of the present invention may be administered by intravenous osmotic pump implantation, and IV infusion. Certain compounds of the present invention when tested as described above may provide a reduction in total infarct volume.

Example 14

Interleukin-1β Microglial Cell Assay

Materials and Equipment
A. Materials for Cell Preparation and Experiment
   Mouse microglial cell line
   DMEM High Glucose media (Gibco Catalog #11965-092)
   FBS (Hyclone Catalog #SH30070.03)
   100× Penicillin/Streptomycin (Gibco Catalog #15140-122).
   LPS (Sigma Catalog #L2537)
   Interferon-gamma (Sigma Catalog #I4777)
   Cell Tracker Green (Molecular Probes Catalog #C2925)
   HBSS buffer (950 ml Pyrogen-free water, 2.44 g/L MgCl2.6H20, 3.73 g/L KCl, 59.58 g/L Hepes, 58.44 g/L NaCl, 1.36 g/L KH2PO4, 1.91 g/L CaCl2.2H2O and pH to 4.5 with HCl)
   Sterile 96-well plates precoated with poly-D-lysine (Corning Catalog #3665)
   96-well deep well mother plate, DyNA Block 1000 (VWR Catalog #40002-008)
B. Materials for Il-1beta Elisa
   Mouse IL-1 beta Duo Set (R & D Systems Catalog #DY401)
   Substrate Solution (R & D Systems Catalog #DY 999)
   Bovine Serum Albumin fraction V (BSA V) (Sigma Catalog #A4503)

| Measurement | Equation | Corrected Value(s) |
|---|---|---|
| Cortical Penumbra (C.P.) | Total Penumbra (T.P.) − Subcortical Penumbra (S.P.) | $T.P._{corr.} = (T.P. \times \% H.S./100)$<br>$C.P._{corr.} = C.P. - (C.P. \times \% H.S./100)$<br>$S.P._{corr.} = S.P. - (S.P. \times \% H.S./100)$ |
| Cortical Infarct | Total Infarct (T.I.) − Subcortical Infarct (S.I.) | $T.I._{corr.} = T.I. - (T.I. \times \% H.S./100)$<br>$S.I._{corr.} = S.I. - (S.I. \times \% H.S./100)$<br>$C.I._{corr.} = C.I. - (C.I. \times \% H.S./100)$ |
| Total Ischemic Damage (T.I.D.) | Total Penumbra + Total Infarct | $T.I.D._{corr.} = T.I.D. - (T.I.D \times \% H.S./100)$ |
| Total Volume (mm$^3$) | Each value is multiplied by 2 (the thickness of the tissue). | |
| Edema Volume | The volumetric differences between the sum of right and left hemispheres determines the edema volume. | |
| % Hemispheric swelling (H.S. | Edema × 100/left hemisphere | |

96-well Costar EIA high binding plates (VWR Catalog #29442-302)
Plate seal (VWR Catalog #29442-310)
PBS (Irvine Scientific Catalog #9240)
Cell Culture Grade Water (Irvine Scientific Catalog #9312)
Tween 20 (Sigma Catalog #P 1379)
Sucrose (Sigma Catalog #S7903)
Sodium Azide (Sigma Catalog #S 8032)
$H_2SO_4$ 5N (VWR Catalog #JT 5691-2)

Experimental Preparation and Procedure:

LPS Activation:

Mouse microglial cells were seeded in poly-D-lysine coated 96-well plates at a density of 10,000 cells/well and allowed to attach for 24 hours. Cells were stimulated by addition of LPS (10 µg/ml) and IFN gamma (10 ng/ml) in the presence or absence of test article. The cells were then incubated for 24 hours at 37° C., after which time the media was removed and used for cytokine determination as described below.

Cell Viability:

Viability of mouse microglial cells after exposure to the test article was determined using a fluorescent viability dye, Cell Tracker Green. Cell Tracker Green was used at a working concentration of 5 µM in 1×HBSS. Cells were washed once with HBSS (200 µl/well) and 100 µl Cell Tracker Green was added to each well. Cells were then incubated at 37° C. for 30 minutes, after which time the Cell Tracker was removed and the cells were washed once with HBSS (200 µl/well). 100 pl fresh HBSS was added to each well and the plate was read on a Fluoroskan plate reader using an excitation wavelength of 485 nm and an emission wavelength of 538 nm.

Mouse IL-1beta Elisa:

Solutions:

Wash Buffer: PBS IL+500 µl Tween 20 (final 0.05%) pH 7.2-7.4.

Blocking Buffer: 500 ml PBS+5 g BSA V (1%)+25 g Sucrose (5%)+0.25 g Sodium Azide (0.05%).

Reagent Diluent: 500 ml PBS+5 g BSA V (1%) pH 7.2-7.4 and filter sterilize through 0.2 µm.

Stop Solution: 2N sulfuric acid.

Duo Set Preparations:

1. The IL-1β capture antibody was reconstituted in 1 ml of PBS to give a final concentration of 720 µg/ml, and the working concentration was 4 µg/ml. For coating one 96-well plate (at 100 µl/well) 56 µl of the 720 µg/ml stock was diluted into 10 ml of PBS.

2. The IL-1β standards were reconstituted in 0.5 ml of Reagent Diluent (70 ng/ml). For a high standard of 1 ng/ml (2 wells at 100 µl each+enough for series dilution) 7.1 µl of the 70 ng/ml standard were diluted into 0.5 ml of Reagent Diluent 3. The IL-1β detection antibody was reconstituted in 1 ml of Reagent Diluent to give a final concentration of 18 pg/ml and the working concentration is 100 ng/ml. For one 96-well plate (at 100 µl/well) 56 µl of the 18 µg/ml stock was diluted into 10 ml of Reagent Diluent.

IL-1.beta ELISA Procedure:

Plate Preparation:

The Costar EIA Hi-binding plate was coated with capture antibody at 4 µg/ml. Each well was coated with 100 µl, and the plate was sealed and incubated overnight at room temperature.

Each well was aspirated and washed 3× with Wash Buffer. Each well was filled to the top, dispensed, and any remaining buffer was removed by inverting the plate and gently blotting against clean paper towels.

Non-specific binding sites were blocked by adding 300 µl of Blocking Buffer to each well, and after sealing incubating for at least 1 hour at room temperature.

After washing the plate was now ready for the samples.

Assay Procedure:

100 µl of either standard or sample were added in each well of the capture-coated and pre-blocked plate. The plate was sealed and incubated for 2 hours at room temperature, followed with washing.

100 µl of the detection antibody (100 ng/ml) were added to each well.

The plate was sealed and incubated at room temperature for 2 hours, followed with washing.

100 µl of the working dilution of Streptavidin-HRP was added, and the plate was sealed and incubated in the dark for 20 minutes at room temperature, followed with washing.

The fresh Substrate Solution was prepared by mixing Color Reagent A ($H_2O_2$) and Color Reagent B (Tetramethylbenzidine) in a 1:1 ratio. 1001 of this Substrate Solution mixture was added to each well and the plate was incubated in the dark for 20 minutes at room temperature.

50 µl of Stop Solution was added to each well, mixing was ensured by gently tapping.

Each plate was read with the Spectramax once at 450 nm.

Results

When tested as described above, compounds of the present invention, such as:

5-[3-(6-Hydroxy-2,7,8-trimethyl-chroman-2-yl)-propylidene]-thiazolidine-2,4-dione;

1-(6-Hydroxy-2,7,8-trimethyl-chroman-2-yl)-3-bis-(5-methyl-2-phenyl-2,4-dihydro-pyrazol-3-one-4-yl)-propane;

5-(4,6-Dimethyl-pyrimidin-2-ylsulfanylmethyl)-2,2,7,8-tetramethyl-chroman-6-ol;

inhibited the IL-1 beta induction with an $EC_{50}$ of 20 µM or less.

Example 15

Rat Paw Edema Assay

Animal Preparation:

Male Sprague-Dawley rats weighing between 175 to 200 g are used in this study. Animals are allowed free access to water and commercial rodent diet under standard laboratory conditions. Room temperature is maintained at 20-23° C. and room illumination is on a 12/12-hour light/dark cycle. Animals are acclimatized to the laboratory environment 5 to 7 days prior to the study.

Experimental Procedure:

Each animal was treated by administration of vehicle, reference or test substance one hour prior to carrageenan injection, as follows:

I.V. Infusion via Femoral Vein: Anesthesia is maintained by inhalation of 3.0% isoflurane (Aerrane, Front Dodge, Iowa) in oxygen throughout the entire procedure. The exterior site of the right femoral vein is shaved and sterilized prior to surgery. A 3-cm incision is made in the right groin region and the femoral vein is isolated. The femoral vein is temporarily ligated with a micro-vascular clip, and a small incision is made on the femoral vein to introduce and advance a polyethylene (PE-50) catheter (Becton. Dickinson and Co., Sparks, Md.). The catheter is secured in place with suture (silk 5/0, Carlisle Laboratories, Farmers Branch, Tex.). The other end of the catheter is attached to a syringe filled with the saline for the bolus injection. Using a hemostat, a pocket is made subcutaneously on the back of the animal so the PE catheter can be brought up to the exteriorization point between the shoulder blade for either a bolus injection or a continuous injection by an osmotic pump.

I.P. Injection: An awake rat is held in a standard hand held position. A 23¾ G needle is injected into the lower right quarter of the abdomen pass the peritoneum, slightly off the midline. To avoid organ injection, the plunger of the syringe is slightly pulled back. If no fluid is withdrawn, the content of the syringe is delivered into the abdominal cavity.

Gavage Feeding: A standard rat gavage tube (Popper & Sons Inc, N.Y.) is attached to a 3-cc hypodermic syringe. The animal is held in a vertical position. The feeding tube is placed into the mouth and then gently advanced until it reached the stomach (the approximate insertion length of the tube should be measured prior to feeding). The content of the syringe is slowly delivered, and then the tube is withdrawn.

One hour post treatment each animal is anesthetized with 3.0% isoflurane (Aerrane, Front Dodge, Iowa) in oxygen and administered 100 µl of 1% Carrageenan Lambda type IV (Sigma Chemical Company, St. Louis, Mo.) suspension in saline, into the intraplantar surface of the right hind paw. Paw edema is measured four hours after carrageenan injection, either by measuring the increase in paw volume using a plethysmometer or the increase in paw weight using a fine scale. Immediately prior to edema measurement, the animals are euthanized via $CO_2$ asphyxiation and 500 µl blood is withdrawn by cardiac puncture for later analysis. Paw volume is determined by the extent to which water is displaced by the paw from a pre-calibrated chamber. The volume of the left hind paw (control) is subtracted from the volume of the right hind paw (carrageenan-treated) to determine the volume of carrageenan-induced edema. To measure the weight difference between paws, both hind paws are removed and weighed separately.

To minimize the variation in the model following steps are taken:
  Carrageenan is made fresh every day prior to the study (2-3 hours before injection).
  The plethysmometer is calibrated each day prior to the study.
  If carrageenan injection causes significant bleeding or a hematoma on the treated foot, the animal is excluded from the study.
  Each paw is marked at the tibio-tarsal joint across the ankle prior to measurements, to ensure each paw was submerged at the same level.
  If reading on the volume needs to be repeated, the paw has to be dried off completely.

Statistical Analysis

The difference of the weight or the volume between right and left paw is calculated for each animal for the analysis. Group data are presented as means+/−SEM and $p<0.05$ are considered significant. Inter-group comparisons are carried out by unpaired student t test (between two groups) or one-way ANOVA followed by post hoc Bonferroni's multiple comparisons.

Results

Certain compounds of the present invention may show significant reduction in edema when tested by this method.

Example 16

Mouse Ear Inflammatory Response to Topical Arachidonic Acid

Animals: Balb C Mice 23-28 gms, from Simonsen Labs, Gilroy, Calif.

Materials:
  Arachidonic Acid, 99% pure from Porcine Liver (Sigma Aldrich) reconstituted in acetone 2 mg/20 ul (200 mg/ml).
  Inhalation anesthesia: Isoflurane 3% (Baxter).
  Blood Sample tubes: Microtainer tubes w/heparin (Becton Dickinson).
  TNFα Elisa assay (R&D Science).

Experimental Procedure

Test compounds, positive control (arachidonic acid only) and standard (Dexamethasone @ 0.1 mg/kg) prepared in solutions of acetone, ethanol or aqueous ethanol, were applied to both sides of the right ear with an Eppendorf repipettor pipette, in a volume of 10 µl each side (20 µl total). 30 Minutes later, 10 µl of arachidonic acid was applied to both sides of the right ear (20 µl total). One hour after the application of arachidonic acid, the mice were deeply anesthetized with isoflurane and a blood sample is taken via the orbital sinuses and placed in Microtainer tubes. The animals were then euthanized by $CO_2$ inhalation and the right ears removed at the base. A uniform plug of ear tissue was obtained using a 8 mm dermal punch. The earplugs were quickly weighed to the nearest 0.1 mg and then flash frozen for TNFα determination.

Statistical Analysis:

Group data was presented as means+/−SEM and $p<0.05$ is considered significant. Inter-group comparisons were carried out by unpaired student t tests (between two groups) or ANOVA (three or more groups) followed by post hoc Dunnet's test.

Results

5-[3-(6-Hydroxy-2,7,8-trimethyl-chroman-2-yl)-propylidene]-thiazolidine-2,4-dione;

showed significant reduction in edema (10 to 70%, $p<0.05$) when tested by this method.

Example 17

High Glutamate-Induced Oxidative Stress Assay (HGOS)

This procedure was used to induce high glutamate-induced oxidative stress (HGOS) in a dopaminergic neuronal cell line. Using this assay the potency and efficacy of test articles against HGOS neuronal cell injury and cell death was established in a high throughput manner.

Materials
  Dopaminergic neuronal cell lines
  DMEM-No Glucose (Life Technologies Cat #11966-025)
  L-glutamine (Life Technologies Cat #25030-081)
  L-glutamic acid, monosodium salt (Sigma Cat #G5889)
  D-glucose (Sigma Cat #G-6151)
  10×HBSS buffer (pH 7.4) (950 ml Pyrogen-free water, 2.44 g/L MgCl2.6H20, 3.73 g/L KCl, 59.58 g/L Hepes, 58.44 g/L NaCl, 1.36 g/L KH2PO4, 1.91 g/L CaCl2.2H2O and pH to 4.5 with HCl)
  Cell Tracker Green fluorescent dye (Molecular Probes, Cat #2925). Prepare a 5 NM solution in pre-warmed HBSS just prior to use.
  Sterile 96-well plates precoated with poly-D-lysine (Corning Catalog #3665)
  96-well deep well mother plate, DyNA Block 1000 (VWR Catalog #40002-008)

Neuronal Cells

The cells were seeded into 96-well plates at a density of 2000 per well and left to grow for 72 hours in a 33° C. incubator with 5% $CO_2$ in air atmosphere. The passage number of the cells for each assay experiment were no later than p11 in order to minimize experimental variation.

Compound Preparation in Deep-Well Mother Plates

VWR Brand DyNA Block 1000, deep well mother plates (VWR Cat. #40002-008) were used for the preparation of the test compounds.

All compounds were dissolved in DMEM-No Glu containing 1 mM glucose, 30 mM glutamate and 1× Pen/Strep. DMEM-No Glu with 1 mM glucose and 1×P/S was used as the negative control, DMEM-No Glucose with 1 mM glucose, 100 M glutamate was used as a positive control and 100 NM Glutathione was added to the positive control as a standard. All of the procedures for this involving the making and dilution of compounds were performed using aseptic conditions and with minimal light.

Cell Preparation

The plates were removed from the incubator and examined under the microscope for morphological appearance and density. Using an aseptic technique and an 8-channel aspirator the media was carefully removed from the cells and replaced with 200 µl of 1×HBSS. This was done as quickly as possible to prevent the cells drying out. The plates were then placed in the humidified 37° C. incubators of the Biomek 2000 Side Loader. Four plates were washed at a time so as to minimize the time that the cells were sitting in 1×HBSS prior to addition of the compound test solution. Experimental Setup The Beckman Biomek workstations were used to load the compounds and controls from the mother plates onto the cell plates that were prewashed with HBSS under sterile conditions. The plates were incubated in the upper HTS incubator at 37° C. in 5% $CO_2$ for exactly 16 hrs. The following day, using the Beckman Biomek workstations, the plates were removed from the incubator. Using Cell Tracker Addition, the compounds were removed from the plates, washed once with 200 µM of pre-warmed 1×HBSS and then 100 µL of 5 µM Cell Tracker Green was added to each well. The plates were incubated at 37° C. for 30 min to allow the dye to enter the cell and be cleaved by the esterases. After washing the cells twice with prewarmed 1×HBSS, the plates were read with the 485 excitation; 538 emission filter pair on a Fluoroskan.

Certain compounds of the present invention such as:
4-(6-Hydroxy-2,2,7,8-tetramethyl-chroman-5-ylmethylene)-2-methyl-5-propyl-2,4-dihydro-pyrazol-3-one,
(6-Hydroxy-2,2,7,8-tetramethyl-chroman-5-ylmethyl)-1-hydroxyurea;
5-(4-Dimethylamino-phenyl)-2,2,7,8-tetramethyl-chroman-6-ol;
5-(4-Methane sulfonyl-phenyl)-2,2,7,8-tetramethyl-chroman-6-ol;
2-(2,2-Dibromo-vinyl)-2,5,7,8-tetramethyl-chroman-6-ol;
2,2,7,8-Tetramethyl-5-pyridin-3-yl-chroman-6-ol;
2,2,7,8-Tetramethyl-5-pyridin-4-yl-chroman-6-ol;
4-(6-Hydroxy-2,2,7,8-tetramethyl-chroman-5-yl)-benzoic acid;
4-(6-Hydroxy-2,2,7,8-tetramethyl-chroman-5-yl)-benzoic acid methyl ester;
2,2,7,8-Tetramethyl-5-phenyl-chroman-6-ol;
5-Cyclopentylsulfanylmethyl-2,2,7,8-tetramethyl-chroman-6-ol;
5-Allylsulfanylmethyl-2,2,7,8-tetramethyl-chroman-6-ol;
5-Hexylsulfanylmethyl-2,2,7,8-tetramethyl-chroman-6-ol;
5-(4,6-Dimethyl-pyrimidin-2-ylsulfanylmethyl)-2,2,7,8-tetramethyl-chroman-6-ol;
1-(6-Hydroxy-2,2,7,8-trimethyl-chroman-2-yl)-3-bis-(5-methyl-2-phenyl-2,4-dihydro-pyrazol-3-one-4-yl)-propane;
5-[3-(6-Hydroxy-2,7,8-trimethyl-chroman-2-yl)-propylidene]-thiazolidine-2,4-dione;
5-[3-(6-Methoxymethoxy-2,7,8-trimethyl-chroman-2-yl)-propylidene]-thiazolidine-2,4-dione; and
1-(3-[6-Hydroxy-2,7,8-trimethyl-2-(4,8,12-trimethyl-tridecyl)-chroman-5-ylmethylsulfanyl]-2-methyl-propionyl)-pyrrolidine-2-carboxylic acid;
were considered to be active when they exhibited protection against HGOS cell injury and cell death with an $EC_{50}$ in a range of less than 5 µM.

Example 18

$LTB_4$-Assay

This procedure was used for measuring the release of the leukotriene LTB4 from a neutrophil cell line using a competitive ELISA technique.

Materials and Equipments

Materials for Cell Preparation and Experiment
    MPRO cell line (ATCC, Catalog #CRL-11422)
    Calciumionophore (A23187) (Sigma, Catalog #C7522)
    Nordihydroguaiaretic acid (NDGA) (BioMol, Catalog #E1101-0001)
    Retinoic Acid (all-trans) (ATRA) (Sigma, Catalog #95152)
    Sterile, tissue-culture treated 96-well plates (Corning, Catalog #3614)

Materials for LTB4 ELISA
    Precoated (Mouse Anti-Rabbit IgG) EIA 96 Well Strip Plates (Cayman, Catalog #400004)
    Leukotriene B4 AChE Tracer (Cayman Catalog #420110)
    Leukotriene B4 EIA Antiserum (Cayman Catalog #420112)
    Ellman's Reagent (Cayman Catalog #400050)
    EIA Buffer Concentrate (10×) (Cayman Catalog #400060)
    Wash Buffer Concentrate (400×) (Cayman Catalog #400062)
    Plastic plate covers (Cayman Catalog #400012)

Procedure

A mouse promyelocytic cell line (MPRO) was used in this assay. These cells are committed immature neutrophils that can be differentiated into mature neutrophils by treatment with 10 µM all-trans retinoic acid for 72 hours Following 72 hours of differentiation, cells were stimulated with 1 µM of a calcium ionophore (A23187) in the presence or absence of test compound or vehicle for 1 hour at 370 C. After this time, supernatant was removed from the cells and the LTB4 levels were determined following manufacturer's instructions, using a Leukotriene B4 EIA kit from Cayman (Cat #520111)

The negative controls were media samples from differentiated but unstimulated cells.

The compounds were screened at 5 concentrations in quadruplicate starting at 10 µM Following the procedure described above certain compounds of the present invention, such as:
5-Allylsulfanylmethyl-2,2,7,8-tetramethyl-chroman-6-ol;
4-(6-Hydroxy-2,2,7,8-tetramethyl-chroman-5-yl)-benzoic acid methyl ester;
4-(6-Hydroxy-2,2,7,8-tetramethyl-chroman-5-yl)-benzoic acid;
2,2,7,8-Tetramethyl-5-pyridin-3-yl-chroman-6-ol;
2-(2,2-Dibromo-vinyl)-2,5,7,8-tetramethyl-chroman-6-ol;
2,2,7,8-Tetramethyl-5-(3-nitro-phenyl)-chroman-6-ol;
2,5,7,8-Tetramethyl-2-thiophen-2-yl-chroman-6-ol;
5-Furan-2-yl-2,2,7,8-tetramethyl-chroman-6-ol;
2-(2,5-Dimethyl-thiophen-3-yl)-2,5,7,8-tetramethyl-chroman-6-ol; and 2-(2,5-Dimethyl-thiophen-3-yl)-2,7,8-trimethyl-chroman-6-ol;

were considered to be active if they exhibited inhibition of LTB4 production with an $EC_{50}$ in a range of less than 1 μM.

Example 19

5-Lipoxygenase Enzyme Assay

This procedure was used for measuring the enzymatic activity of human recombinant 5-lipoxygenase using a colorimetric method based on the ferric oxidation of xylenol orange.

Materials
  96 well flat bottom microfilter plates (VWR, Catalog #62402-933 9295)
  Lipoxygenase screening assay buffer (Cayman, Catalog #760710)
  Human recombinant 5-lipoxygenase (Cayman, Catalog #60402)
  Arachidonic Acid (Sigma, Catalog #A3555)
  Xylenol orange tetrasodium salt (Aldrich, Catalog #227854)
  Iron (II) sulfate heptahydrate (Sigma, Catalog #F7002)
  Sulfuric acid (95-98%) [18M]-Methanol Procedure Human recombinant 5-lipoxygenase (Cayman Cat #60402) was used in this assay. The test compound and/or vehicle was added to 0.51-1 5-lipoxygenase in 50 mM Tris-HCl buffer, pH 7.4. The reaction was initiated by addition of 70 μM arachidonic acid in Tris-HCl buffer, pH 7.4, and terminated after a 10 minute incubation at room temperature by addition of FOX reagent (25 mM sulphuric acid, 100 μM xylenol orange, 100 μM iron (II) sulphate, methanol:water 9:1). The yellow color of acidified xylenol orange was converted to a blue color by the lipid hydroperoxide-mediated oxidation of Fe 2+ ions and the interaction of the resulting Fe 3+ ions with the dye. The complex was allowed to form during a 1 hour incubation at room temperature with shaking. Absorbance of the Fe 3+ complex was then measured at 620 nM using a spectrophotometer.

Negative controls contained enzyme during the incubation step but substrate was not added until after the FOX reagent.

Compounds were screened at 5 concentrations in triplicate starting at 10 μM

Certain compounds of the present invention such as:
5-Allyl[sulfany[methyl-2,2,7,8-tetramethyl-chroman-6-ol;
2-(2,2-Dibromo-vinyl)-2,5,7,8-tetramethyl-chroman-6-ol;
5-(4-Chloro-phenyl)-2,2,7,8-tetramethyl-chroman-6-ol;
5-(4-tert-Butyl-phenyl)-2,2,7,8-tetramethyl-chroman-6-ol;
2,2,7,8-Tetramethyl-5-(3,4,5-trimethoxy-phenyl)-chroman-6-ol;
5-(6-Hydroxy-2,2,7,8-tetramethyl-chroman-5-yl)-2,3-dimethyl-benzene-1,4-diol;
2,5,7,8-Tetramethyl-2-thiophen-2-yl-chroman-6-ol;
5-Furan-2-yl-2,2,7,8-tetramethyl-chroman-6-ol;
2-(2,5-Dimethyl-thiophen-3-yl)-2,5,7,8-tetramethyl-chroman-6-ol;
2-(2,5-Dimethyl-thiophen-3-yl)-2,7,8-trimethyl-chroman-6-ol; and
2-(2,2-Dich[oro-vinyl)-2,5,7,8-tetramethyl-chroman-6-ol;
were considered to be active when they exhibited inhibition of 5-Lipoxygenase with an $IC_{50}$ in a range of less than 1 μM.

Example 20

12/15-Lipoxygenase Enzyme Assay

This procedure was used for measuring the enzymatic activity of porcine leukocyte 12/15-lipoxygenase using a colorimetric method based on the ferric oxidation of xylenol orange.

Materials
  96 well flat bottom microfilter plates (VWR, Catalog #62402-933 9295)
  Lipoxygenase screening assay buffer (Cayman, Catalog #760710)
  Porcine leukocyte 12/15-lipoxygenase (Cayman, Catalog #60300)
  Arachidonic Acid (Sigma, Catalog #A3555)
  Xylenol orange tetrasodium salt (Aldrich, Catalog #227854)
  Iron (II) sulfate heptahydrate (Sigma, Catalog #F7002)
  Sulfuric acid (95-98%) [18M]
  Methanol Procedure Porcine Leukocyte 12/15-lipoxygenase (Cayman Cat #60300) was used in this assay. Test compound and/or vehicle was added to 1.3 U 12/15-lipoxygenase in 50 mM Tris-HCl buffer, pH 7.4. The reaction was initiated by addition of 70 μM arachidonic acid in Tris-HCl buffer, pH 7.4, and terminated after a 10 minute incubation at room temperature by addition of FOX reagent (25 mM sulphuric acid, 100 μM xylenol orange, 100 μM iron (II) sulphate, methanol:water 9:1). The yellow color of acidified xylenol orange was converted to a blue color by the lipid hydroperoxide-mediated oxidation of Fe 2+ ions and the interaction of the resulting Fe 3+ ions with the dye. The complex was allowed to form during a 1 hour incubation at room temperature with shaking. Absorbance of the Fe 3+ complex was then measured at 620 nM using a spectrophotometer.

Negative controls contained enzyme during the incubation step but substrate was not added until after the FOX reagent.

Compounds are screened at 5 concentrations in triplicate starting at 10 μM

Certain compounds of the present invention such as:
5-Allylsulfanylmethyl-2,2,7,8-tetramethyl-chroman-6-ol;
5-(5-Chloro-3-methyl-pent-2-enyl)-2,2,7,8-tetramethyl-chroman-6-ol;
4-(6-Hydroxy-2,2,7,8-tetramethyl-chroman-5-yl)-benzoic acid methyl ester;
2-(2,2-Dibromo-vinyl)-2,5,7,8-tetramethyl-chroman-6-ol;
2,5,7,8-Tetramethyl-2-thiophen-2-yl-chroman-6-ol;
5-Furan-2-yl-2,2,7,8-tetramethyl-chroman-6-ol;
2-(2,5-Dimethyl-thiophen-3-yl)-2,5,7,8-tetramethyl-chroman-6-ol;
2-(2,2-Dichloro-vinyl)-2,5,7,8-tetramethyl-chroman-6-ol;
8-Chloro-2-(2,5-dimethyl-thiophen-3-yl)-2,5,7-trimethyl-chroman-6-ol;
5-Chloro-2,7,8-trimethyl-2-thiophen-2-yl-chroman-6-ol; and
2-(3-Chloro-propyl)-5,7-dimethyl-2-thiophen-2-yl-chroman-6-ol;
were considered to be active when they exhibited inhibition of 12/15-Lipoxygenase with an $IC_{50}$ in a range of less than 1 μM.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. All patents and publications cited above are hereby incorporated by reference.

What is claimed is:

1. A compound represented by Formula I

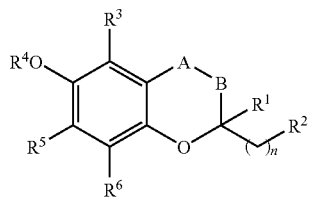

Formula I wherein:

-A-B— is —$CH_2$—$CH_2$—, —CH=CH—, —$CH_2$—O—, or —$CH_2$—S—;

n is 0;

$R^1$ is $C_{1-4}$ alkyl;

$R^2$ is $C_{1-4}$ alkyl;

$R^3$ is cycloalkyl, aryl, or saturated, partially unsaturated or unsaturated heterocyclyl, all rings optionally substituted with one or more substituents selected from alkyl, haloalkyl, hydroxy, alkoxy, halogen, oxo, cyano, nitro, amino, —$SO_2NR_2$, and —C(O)OR, with the proviso that the heterocyclyl is not substituted or unsubstituted 4,5-dihydro-isoxazol-3-yl or substituted or unsubstituted chroman; or haloalkenyl;

$R^4$ is hydrogen, optionally substituted $C_{1-4}$ alkyl, $C_{2-12}$ alkenyl, hydroxyalkyl, acyl, glucoside, phosphoryl, phosphoryloxyalkyl, carboxyalkylcarbonyl, aminoalkylcarbonyl, or alkylketocarbonyl;

$R^5$ and $R^6$ are independently of each other $C_{1-6}$ alkyl, $C_{2-12}$ alkenyl, or halogen; and R is hydrogen or $C_{1-4}$ alkyl;

or single stereoisomers, mixtures of stereoisomers, or pharmaceutically acceptable salts thereof.

2. The compound of claim 1, wherein $R^5$ and $R^6$ are $C_{1-4}$ alkyl and $R^4$ is hydrogen.

3. The compound of claim 2, wherein $R^1$, $R^2$, $R^5$ and $R^6$ are methyl and $R^4$ is hydrogen.

4. The compound of claim 1, wherein $R^3$ is aryl or saturated, partially saturated or unsaturated heterocyclyl both optionally substituted with one or more substituents selected from alkyl, haloalkyl, hydroxy, alkoxy, halogen, oxo, cyano, nitro, amino, —$SO_2NR_2$, and —C(O)OR.

5. The compound of claim 4, selected from:

5-(4-Methoxy-phenyl)-2,2,7,8-tetramethyl-chroman-6-ol;
2,2,7,8-Tetramethyl-5-phenyl-chroman-6-ol;
4-(6-Hydroxy-2,2,7,8-tetramethyl-chroman-5-yl)-benzoic acid methyl ester;
4-(6-Hydroxy-2,2,7,8-tetramethyl-chroman-5-yl)-benzoic acid;
2,2,7,8-Tetramethyl-5-pyridin-4-yl-chroman-6-ol;
2,2,7,8-Tetramethyl-5-pyridin-3-yl-chroman-6-ol;
5-(4-Methanesulfonyl-phenyl)-2,2,7,8-tetramethyl-chroman-6-ol;
5-(4-Dimethylamino-phenyl)-2,2,7,8-tetramethyl-chroman-6-ol;
5-(4-Chloro-phenyl)-2,2,7,8-tetramethyl-chroman-6-ol;
4-(6-Hydroxy-2,2,7,8-tetramethyl-chroman-5-yl)-benzenesulfonamide;
2,2,7,8-Tetramethyl-5-(3-nitro-phenyl)-chroman-6-ol;
2,2,7,8-Tetramethyl-5-(4-trifluoromethyl-phenyl)-chroman-6-ol;
5-(4-tert-Butyl-phenyl)-2,2,7,8-tetramethyl-chroman-6-ol;
2,2,7,8-Tetramethyl-5-(3,4,5-trimethoxy-phenyl)-chroman-6-ol;
5-(2,5-Dimethoxy-3,4-dimethyl-phenyl)-2,2,7,8-tetramethyl-chroman-6-ol;
4-(6-Hydroxy-2,2,7,8-tetramethyl-chroman-5-yl)-benzonitrile;
5-(2,5-Dimethoxy-3,4-dimethyl-phenyl)-2,2,7,8-tetramethyl-chroman-6-ol;
5-(6-Hydroxy-2,2,7,8-tetramethyl-chroman-5-yl)-benzene-1,2,3-triol;
5-(6-Hydroxy-2,2,7,8-tetramethyl-chroman-5-yl)-2,3-dimethyl-benzene-1,4-diol;
5-(2-Chloro-phenyl)-2,2,7,8-tetramethyl-chroman-6-ol;
5-Furan-2-yl-2,2,7,8-tetramethyl-chroman-6-ol;
and single stereoisomers, mixtures of stereoisomers, or pharmaceutically acceptable salts thereof.

6. A pharmaceutical composition comprising a compound of claim 1 admixed with a pharmaceutically acceptable excipient.

7. The compound of claim 1, where aryl is substituted phenyl or unsubstituted phenyl.

8. The compound of claim 4, where aryl is substituted phenyl or unsubstituted phenyl.

9. The compound of claim 1, where -A-B— is —$CH_2$—$CH_2$—.

10. The compound of claim 4, where -A-B— is —$CH_2$—$CH_2$—.

11. The compound of claim 5, selected from 2,2,7,8-Tetramethyl-5-(3-nitro-phenyl)-chroman-6-ol;
and single stereoisomers, mixtures of stereoisomers, or pharmaceutically acceptable salts thereof.

* * * * *